US010541652B2

(12) United States Patent
Finlinson et al.

(10) Patent No.: US 10,541,652 B2
(45) Date of Patent: Jan. 21, 2020

(54) APPARATUS AND METHOD FOR FILTER SETTLING CALIBRATION TO IMPROVE SPEED OF TRACKING AND CANCELLING OF DC OFFSET

(71) Applicant: Intel Corporation, Santa Clara, CA (US)

(72) Inventors: Craig P. Finlinson, Chippenham (GB); Nicholas P. Cowley, Wroughton (GB); Mark S. Mudd, Wootten Bassett (GB)

(73) Assignee: Intel Corporation, Santa Clara, CA (US)

( * ) Notice: Subject to any disclaimer, the term of this patent is extended or adjusted under 35 U.S.C. 154(b) by 663 days.

(21) Appl. No.: 14/752,879

(22) Filed: Jun. 27, 2015

(65) Prior Publication Data
US 2016/0380595 A1  Dec. 29, 2016

(51) Int. Cl.
H03F 1/02 (2006.01)
H03G 1/00 (2006.01)
H03K 5/003 (2006.01)
A61B 5/024 (2006.01)
A61B 5/145 (2006.01)

(52) U.S. Cl.
CPC ....... H03F 1/0227 (2013.01); A61B 5/02416 (2013.01); A61B 5/14542 (2013.01); H03G 1/0029 (2013.01); H03K 5/003 (2013.01); H03F 2203/45116 (2013.01)

(58) Field of Classification Search
CPC ............... H03F 1/0227; H03F 3/45968; H03F 3/45475; H03F 2203/45048; H03F 2203/45116; A61B 5/14542; A61B 5/02416; H03G 1/0029; H03K 5/003
See application file for complete search history.

(56) References Cited

U.S. PATENT DOCUMENTS

| 7,176,652 | B2 | 2/2007 | Wakabayashi et al. |
|---|---|---|---|
| 2002/0101270 | A1 | 9/2002 | Nishizono et al. |
| 2004/0215095 | A1 | 10/2004 | Lee et al. |
| 2005/0025259 | A1 | 2/2005 | Miyasita |
| 2005/0187452 | A1 | 8/2005 | Petersen et al. |
| 2008/0061872 | A1* | 3/2008 | Hughes ............... H03F 3/45475 330/86 |
| 2009/0110015 | A1 | 4/2009 | Heink et al. |
| 2012/0098454 | A1 | 4/2012 | Grotkowski |

(Continued)

FOREIGN PATENT DOCUMENTS

| JP | 2004194908 | 7/2004 |
|---|---|---|
| KR | 1020060096842 | 9/2006 |
| WO | 2016000986 | 1/2016 |

OTHER PUBLICATIONS

Restriction Requirement for U.S. Appl. No. 14/752,881, dated Jul. 11, 2017.

(Continued)

Primary Examiner — Michael W Kahelin
(74) Attorney, Agent, or Firm — Green, Howard & Mughal LLP

(57) ABSTRACT

Described is an apparatus which comprises: an amplifier to receive a reference voltage; and calibration logic which is operable to receive a first voltage and to provide the reference voltage to the amplifier, wherein the calibration logic is operable to generate a look-up table (LUT) that maps the first voltage to a drive current.

18 Claims, 18 Drawing Sheets

(56) References Cited

U.S. PATENT DOCUMENTS

2014/0275852 A1     9/2014    Hong et al.
2016/0235313 A1     8/2016    Sharma

OTHER PUBLICATIONS

International Preliminary Report on Patentability dated Sep. 7, 2018 for PCT Patent Application No. PCT/US17/13801.
Notice of Allowance dated Nov. 16, 2018 for U.S. Appl. No. 15/050,306.
Restriction Requirement dated Oct. 25, 2018 for U.S. Appl. No. 14/752,881.
International Search Report and Written Opinion for International Patent Application No. PCT/US2017/013801, dated Apr. 20, 2017.
Non-Final Office Action for U.S. Appl. No. 15/050,306, dated May 10, 2018.
Restriction Requirement for U.S. Appl. No. 15/050,306, dated Nov. 16, 2017.
Glaros, K. et al., "A Sub-mW Fully-Integrated Pulse Oximeter Front-End", IEEE Transactions on Biomedical Circuits and Systems, Vol. 7, No. 3, Jun. 2013.
Hayes, M. et al., "A New Method for Pulse Oximetry Possessing Inherent Insensitivity to Artifact", IEEE Transactions on Biomedical Circuits and Systems, vol. 7, No. 3, Jun. 2013, pp. 452-461.
Patterson, J. et al., "Ratiometric Artifact Reduction in Low Power Reflective Photoplethysmography", IEEE Transactions on Biomedical Circuits and Systems, vol. 7, No. 3, Jun. 2013, pp. 330-338.
Wong, A. et al., "A Low-Power CMOS Front-End for Photoplethysmographic Signal Acquisition With Robust DC Photocurrent Rejection", IEEE Transactions on Biomedical Circuits and Systems, vol. 2, No. 4, Dec. 2008, pp. 280-288.
Non-Final Office Action dated Apr. 10, 2019 for U.S. Appl. No. 14/752,881.

\* cited by examiner

Fig. 10B

APPARATUS AND METHOD FOR FILTER SETTLING CALIBRATION TO IMPROVE SPEED OF TRACKING AND CANCELLING OF DC OFFSET

BACKGROUND

Photoplethysmography (PPG) based heart rate detection works by detecting reflected light from blood vessels as the blood vessels dilate and contract in sympathy with changing blood pressure associated with the heartbeat. The light is generated by a pulsed Light Emitting Diode (LED) which is placed against the skin (often a wrist) and detected by a photodiode also placed against the skin in near vicinity to the LED. Since the LED has a wide transmission angle and the emitted light is subject to scattering within the body, light reflects to the photodiode from extraneous sources such as bones as well as from the blood vessels. The signal component obtained from the light reflected from extraneous sources is commonly referred to as the DC component of the received signal.

The undesired DC reflected component received is significantly greater than the signal from the blood vessel (e.g., the DC reflected component may be over 80 dB greater than the signal of interest which may typically be just 400 pA). The undesired DC component presents a number of issues. For example, amplifying the input signal to provide sufficient gain to the desired signal to detect it may lead to saturation in the amplifier stages of the PPG device.

PPG devices may wobble during use. As such, variable motion artifacts are introduced into the received photocurrents making tracking of the desired signal from the undesired signal difficult. One way to track the signal of interest from other undesirable received signals is to use a low gain, high bandwidth amplifier chain to avoid clipping (e.g., signal collapsing to ground), followed by an oversampling Analog-to-Digital Converter (ADC) (e.g., 22-bit ADC). This approach is brute-force and sub-optimal because it requires extra averaging, power burning, and is slow.

BRIEF DESCRIPTION OF THE DRAWINGS

The embodiments of the disclosure will be understood more fully from the detailed description given below and from the accompanying drawings of various embodiments of the disclosure, which, however, should not be taken to limit the disclosure to the specific embodiments, but are for explanation and understanding only.

FIG. 10B illustrates a table of light source drive current and photodiode current for the eighteen steps of the calibration example of FIG. 10A using the apparatus according to some embodiments.

DETAILED DESCRIPTION

Figure 1:
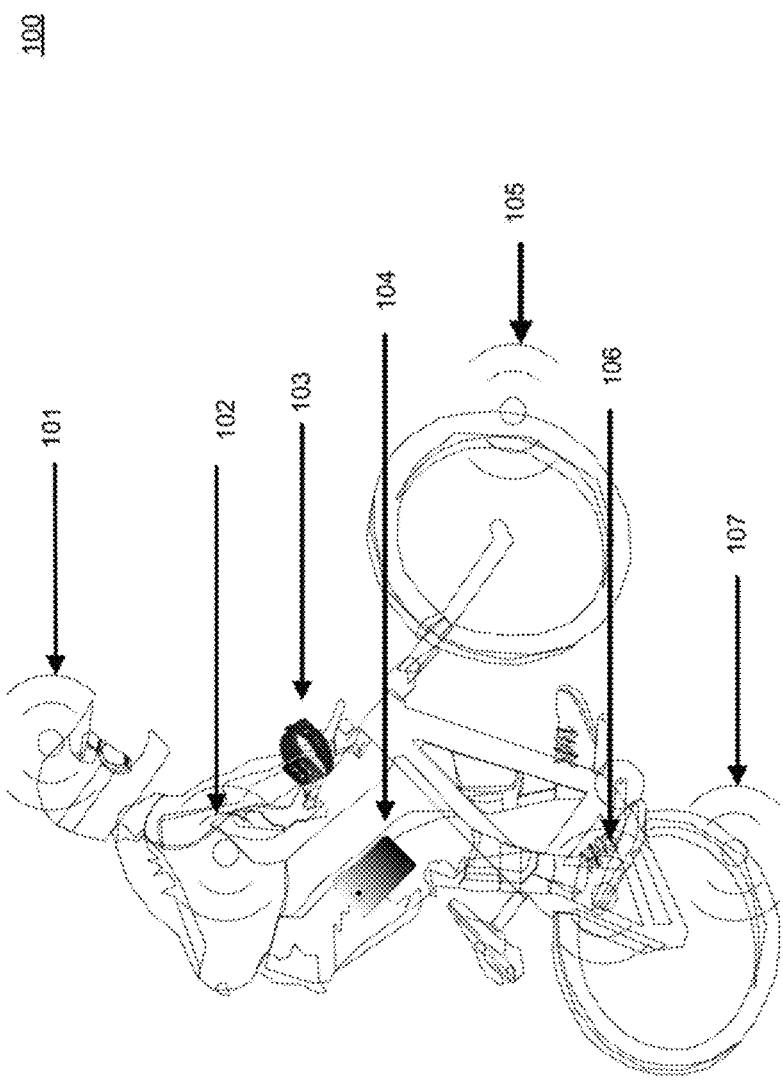
FIG. 1 illustrates an ensemble of wearable devices including a Photoplethysmography (PPG) device with apparatus to calibrate filter settling time and improve speed of tracking and cancelling of DC offset, according to some embodiments of the disclosure.

Market potential in the emerging wearable wellness and sports monitoring space is vast. Accurate integrated heart-rate and blood oxygen measurement circuitry is a vital part of increasing market share. A significant challenge for the present and the future is the fast and robust acquisition of cardiac waveforms from photodiodes using photoplethysmography or photoplethysmogram (PPG). PPG is an optically obtained volumetric measurement of an organ. Using traditional PPG measurement technology in wearable devices is non-optimal because they consume high power and circuit area. Additionally, wrist based wearable devices may introduce sharp motions due to user's wrist motion.

Some embodiments provide an apparatus and method to cancel the DC component, generated by the photodiode, by exploiting the DC component to generate a feedforward cancellation signal which is applied to an input of an amplifier (e.g., an amplifier configured as transimpedance amplifier (TIA)). While various embodiments are described with reference to a particular offset cancelling frontend circuit (e.g., a frontend circuit that exploits the DC component to generate a feedforward cancellation signal which is applied to an input of an amplifier), it can be altered for other offset cancelling frontends that may result in different circuits. However, the overall transfer function mapping principal described with reference to various embodiments remains the same.

Continuing with the example of the PPG device, since the LED has a wide transmission angle and the emitted light is subject to scattering within the body, light reflects to the photodiode from extraneous sources such as bones as well as from the blood vessels. The undesired DC reflected component received is significantly greater than the signal from the blood vessel (e.g., the DC reflected component may be over 80 dB greater than the signal of interest which may be typically just 400 pA). The undesired DC component presents a number of issues. For example, amplifying the input signal to provide sufficient gain to the desired signal to detect it may lead to saturation in the amplifier stages of the PPG device.

To remove the undesired DC component, a slow analog filter (e.g., a low-pole frequency filter such as sample and hold filter 302 described with reference to FIG. 3A and other figures) may be used. The settling of the output of this filter increases the signal acquisition time of the PPG device/system. As such, the low frequency pole filter can be a speed limiter in cancelling the DC component (or offset).

For example, the output of the filter may take a large amount of time to settle to a steady state condition after a pulsed current is generated by the photodiode. Here, the pulsed current corresponds to the pulsed on/off operation of the light source (e.g., an LED) that shines light on the media (e.g., human wrist) whose condition (e.g., pulse rate or heartbeat) is being detected (e.g., acquired or computed).

The undesired DC component may step up/down or change regularly as a wider digital control system chooses to adjust intensity of the LED during operation. In some embodiments, this DC component is estimated in advance and the output of the filter is driven with an initial voltage level. As such, the process of cancelling this DC component is accelerated (i.e., improved).

The various embodiments here are described with reference to accelerating the settling of the output of the low frequency pole filter (or low pass sample-hold filter) for fast acquisition of the PPG signal. However, the embodiments can be used for accelerating the settling time of any filter for any use. In some embodiments, a transfer function mapping is established for subsequent initialization of the filter (i.e., the low frequency pole filter or low pass sample-hold filter). In some embodiments, another transfer function mapping is established using an injected DC current to improve the performance (i.e., gain and/or offset handling) of the PPG system.

In some embodiments, a calibration cycle is used in the presence of an unknown stimulus (e.g., light reflected off) from a user's skin during normal use. In some embodiments, during calibration, at least two signals are present which are separated. These two signals are an unknown signal (e.g., current from a current source such as a photodiode corresponding to the reflected light) of low and finite bandwidth (which should not influence the DC calibration) and a deliberately injected high frequency component that can be controlled, separated, and observed during calibration.

This type of calibration is useful as it can happen in-situ on a user's wrist whilst acquiring PPG information (such as pulse rate, heartbeat, etc.). This type of calibration can used to make or estimate predictions for future filter output states depending on the attained transfer function to the high frequency injected signal. In some embodiments, using this transfer function, a fixed DC offset correction component can be estimated and injected to help subsequent frontend circuits cope with a larger DC range. Other technical effects will be evident from the description of illustrations of the various embodiments.

In the following description, numerous details are discussed to provide a more thorough explanation of embodiments of the present disclosure. It will be apparent, however, to one skilled in the art, that embodiments of the present disclosure may be practiced without these specific details. In other instances, well-known structures and devices are shown in block diagram form, rather than in detail, in order to avoid obscuring embodiments of the present disclosure.

Note that in the corresponding drawings of the embodiments, signals are represented with lines. Some lines may be thicker, to indicate more constituent signal paths, and/or have arrows at one or more ends, to indicate primary information flow direction. Such indications are not intended to be limiting. Rather, the lines are used in connection with one or more exemplary embodiments to facilitate easier understanding of a circuit or a logical unit. Any represented signal, as dictated by design needs or preferences, may actually comprise one or more signals that may travel in either direction and may be implemented with any suitable type of signal scheme.

Throughout the specification, and in the claims, the term "connected" means a direct connection, such as electrical, mechanical, or magnetic connection between the things that are connected, without any intermediary devices. The term "coupled" means a direct or indirect connection, such as a direct electrical, mechanical, or magnetic connection between the things that are connected or an indirect connection, through one or more passive or active intermediary devices. The term "circuit" or "module" may refer to one or more passive and/or active components that are arranged to cooperate with one another to provide a desired function. The term "signal" may refer to at least one current signal, voltage signal, magnetic signal, or data/clock signal. The meaning of "a," "an," and "the" include plural references. The meaning of "in" includes "in" and "on."

The terms "substantially," "close," "approximately," "near," and "about," generally refer to being within +/−10% of a target value. Unless otherwise specified the use of the ordinal adjectives "first," "second," and "third," etc., to describe a common object, merely indicate that different instances of like objects are being referred to, and are not intended to imply that the objects so described must be in a given sequence, either temporally, spatially, in ranking or in any other manner.

For purposes of the embodiments, the transistors in various circuits, modules, and logic blocks are metal oxide semiconductor (MOS) transistors, which include drain, source, gate, and bulk terminals. The transistors also include Tri-Gate and FinFET transistors, Gate All Around Cylindrical Transistors, Tunneling FET (TFET), Square Wire, or Rectangular Ribbon Transistors or other devices implementing transistor functionality like carbon nano tubes or spintronic devices. MOSFET symmetrical source and drain terminals i.e., are identical terminals and are interchangeably used here. A TFET device, on the other hand, has asymmetric Source and Drain terminals. Those skilled in the art will appreciate that other transistors, for example, Bi-polar junction transistors—BJT PNP/NPN, BiCMOS, CMOS, eFET, etc., may be used without departing from the scope of the disclosure.

FIG. 1 illustrates an ensemble 100 of wearable devices including a PPG device with apparatus to calibrate filter settling time and improve speed of tracking and cancelling of DC offset, according to some embodiments of the disclosure. In this example, ensemble 100 is on a person and his/her ride (here, a bicycle). However, the embodiments are not limited to such. Other scenarios of wearable devices and their usage may work with the various embodiments.

For example, PPG device with apparatus to calibrate filter settling time and improve speed of tracking and cancelling of DC offset can be embedded into some other products (e.g., medical devices, ambulances, patient uniform, doctor's uniform, etc.) and can be controlled using a controller or a terminal device. The PPG device with apparatus to calibrate filter settling time and to improve speed of tracking and cancelling of DC offset of some embodiments can also be part of a wearable device. The term "wearable device" (or wearable computing device) generally refers to a device coupled to a person. For example, devices (such as sensors, cameras, speakers, microphones (mic), smartphones, smart watches, medical devices, etc.) which are directly attached on a person or on the person's clothing are within the scope of wearable devices.

In some examples, wearable computing devices may be powered by a main power supply such as an AC/DC power outlet. In some examples, wearable computing devices may be powered by a battery. In some examples, wearable computing devices may be powered by a specialized external source based on Near Field Communication (NFC). The specialized external source may provide an electromagnetic field that may be harvested by circuitry at the wearable computing device. Another way to power the wearable computing device is electromagnetic field associated with wireless communication, for example, WLAN (Wireless Local Area Network) transmissions. WLAN transmissions use far field radio communications that have a far greater range to power a wearable computing device than NFC transmission. WLAN transmissions are commonly used for wireless communications with most types of terminal computing devices.

For example, the WLAN transmissions may be used in accordance with one or more WLAN standards based on Carrier Sense Multiple Access with Collision Detection (CSMA/CD) such as those promulgated by the Institute of Electrical Engineers (IEEE). These WLAN standards may be based on CSMA/CD wireless technologies such as Wi-Fi™ and may include Ethernet wireless standards (including progenies and variants) associated with the IEEE 802.11-2012 Standard for Information technology—Telecommunications and information exchange between systems—Local and metropolitan area networks—Specific requirements Part 11: WLAN Media Access Controller (MAC) and Physical Layer (PHY) Specifications, published March 2012, and/or later versions of this standard ("IEEE 802.11").

Continuing with the example of FIG. 1, ensemble 100 of wearable devices includes device 101 (e.g., camera, microphone, etc.) on a helmet, device 102 (e.g., PPG device with apparatus to calibrate filter settling time and improve speed of tracking and cancelling of DC offset, where the PPG device can be a pulse sensor, heartbeat sensor, blood oxygen level sensor, blood pressure sensor, or any other sensor such as those used in the fields of ECG (electrocardiography), EMG (electromyography), EOG (electrooculography, which is a detection of current associated with movement of the eyeball), ENG (electronystagmography), etc.) on the person's arm, device 103 (e.g., a smart watch that can function as a terminal device, controller, or a device to be controlled), device 104 (e.g., a smart phone and/or tablet in a pocket of the person's clothing), device 105 (e.g., pressure sensor to sense or measure pressure of a tire, or gas sensor to sense nitrogen air leaking from the tire), device 106 (e.g., an accelerometer to measure paddling speed), device 107 (e.g., another pressure sensor for the other tire). In some embodiments, PPG device is embedded in device 103 (e.g., smart watch). PPG device can also be embedded in other devices. In some embodiments, ensemble 100 of wearable devices has the capability to communicate by wireless energy harvesting mechanisms or other types of wireless transmission mechanisms.

In some embodiments, device 102 comprises PPG device with apparatus to calibrate filter settling time and improve speed of tracking and cancelling of DC offset. In some embodiments, in a PPG application, a light source (e.g., a LED) shines light into a user's skin under a wearable device (e.g., a smartwatch). In some embodiments, this light is shone at low duty cycles to save power (i.e., a short duration pulse to minimise power dissipation). Duty cycle is the ratio of on to off events (i.e., ratio of logic 1 to logic 0 etc.). The repetition rate of the pulse may be a few tens of Hertz to up to a few kHz, in accordance with some embodiments. A person skilled in the art would appreciate that the higher the frequency (i.e., the repetition rate of the pulse) the better the resolution but the more the current consumed.

In some embodiments, the PPG device comprises a current source that activates by light (e.g., a photodiode) which generates an output current in response to the received light, where the output current has both the desired AC component and the undesired component such as DC plus motion artifacts. Generally, the DC component is less than 0.5 Hz and the desired AC component is in the range of 0.5 Hz to 20 Hz (e.g., the frequency of blood modulation under the skin) However, the embodiments are applicable to other values of AC and DC components.

The received light is the light reflected or scattered off the bones and/or blood vessels under the user's skin. In some embodiments, the received light is detected by a photodetector in a narrow pulsed time window and is then conditioned, amplified, and converted to a digital signal so digital signal processing can be applied and the heartrate and/or other data can be extracted. In some embodiments, the PPG device includes a current-to-voltage (I-to-V) converter which receives the output current from the photodiode, and generates an output voltage proportional to the input current (i.e., current from the photodiode). In some embodiments, the output voltage is inversely proportional to the input current. More current may imply a greater amplitude output signal though there may be an inversion in sense. In some embodiments, a sample-and-hold (or a track and hold) filter is used to remove the AC component and to store the DC component.

In some embodiments, this stored DC component (e.g., stored in a switching capacitor) becomes a reference voltage for an amplifier configured as a transimpedance amplifier (TIA). As such, the undesired DC component is exploited to generate a feedforward cancellation signal which is applied to the non-inverting input of the TIA, and so the DC offset is cancelled at the output and moved instead to the input. In some embodiments, the PPG device includes a voltage-to-current converter which establishes the TIA output at the level of the DC component. As such, slewing in the TIA is reduced upon receiving a next pulse of current from the photodiode. Various embodiments here are described with reference to the amplifier being a TIA. However, other implementations are also possible.

In some embodiments, device 102 has a calibration logic which is operable to map a transfer function for subsequent initialization of the sample-and-hold filter. In some embodiments, the calibration logic is operable to exploit the control over the LED current and the received current (e.g., from the photodiode) to map transfer function of the reflective medium (i.e., current in and current/voltage out). In some embodiments, the calibration logic is operable to use this information (i.e., the transfer function) to digitally hold a look-up table (LUT) of the predicted photo currents. In some embodiments, the calibration logic is operable to apply this LUT to an offset cancelling frontend to initialize the filter to hold the correct DC value for the selected LED current.

In some embodiments, device 102 has an enhanced calibration logic which is operable to take advantage of the transfer function mapping to improve the performance of the PPG device 102 (i.e., improve gain and/or offset handling). In some embodiments, the enhanced calibration logic incorporates a coarse DC current injected straight to the photodiode during transfer function mapping. This current is injected when clipping due to too large a photocurrent as seen by the ADC codes is received (in this case clipping is when $I_{photodiode}$ is greater than $I_{ref}$, where $I_{photodiode}$ is the current generated by the photodiode while $I_{ref}$ is the reference current of the current-to-voltage converter). In some embodiments, the coarse DC current can be added either incrementally or in Successive Approximation Register (SAR) style to re-center the readings of the current-to-voltage converter.

In some embodiments, compared to the LUT generated by the calibration logic, the transfer function mapping LUT generated by the enhanced calibration logic shows both the filter voltage (to set for enhanced acquisition speed) and also the DC current to inject to avoid clipping (for enhancing gain and/or offset handling) for every LED current chosen.

One technical effect of the enhanced calibration logic is that Rf (i.e., the feedback resistor between the output of the TIA and the input of the TIA) can be made much larger than in prior art in design to give more transimpedance gain. Also the linear range of the offset correction circuitry can now be many times larger as not all current will need to flow back through resistor Rf. Other technical effects of the enhanced calibration logic will be evident from the various embodiments and illustrations.

In some embodiments, the PPG device includes an antenna to transmit the processed data (e.g., the digitized data in modulated form from the output of the TIA) to a controller or a terminal device (e.g., a smart phone, laptop, cloud, etc.) for further processing. In some embodiments, the antenna may comprise one or more directional or omni-directional antennas, including monopole antennas, dipole antennas, loop antennas, patch antennas, microstrip antennas, coplanar wave antennas, or other types of antennas suitable for transmission of Radio Frequency (RF) signals. In some multiple-input multiple-output (MIMO) embodiments, the antennas are separated to take advantage of spatial diversity.

Figure 2:
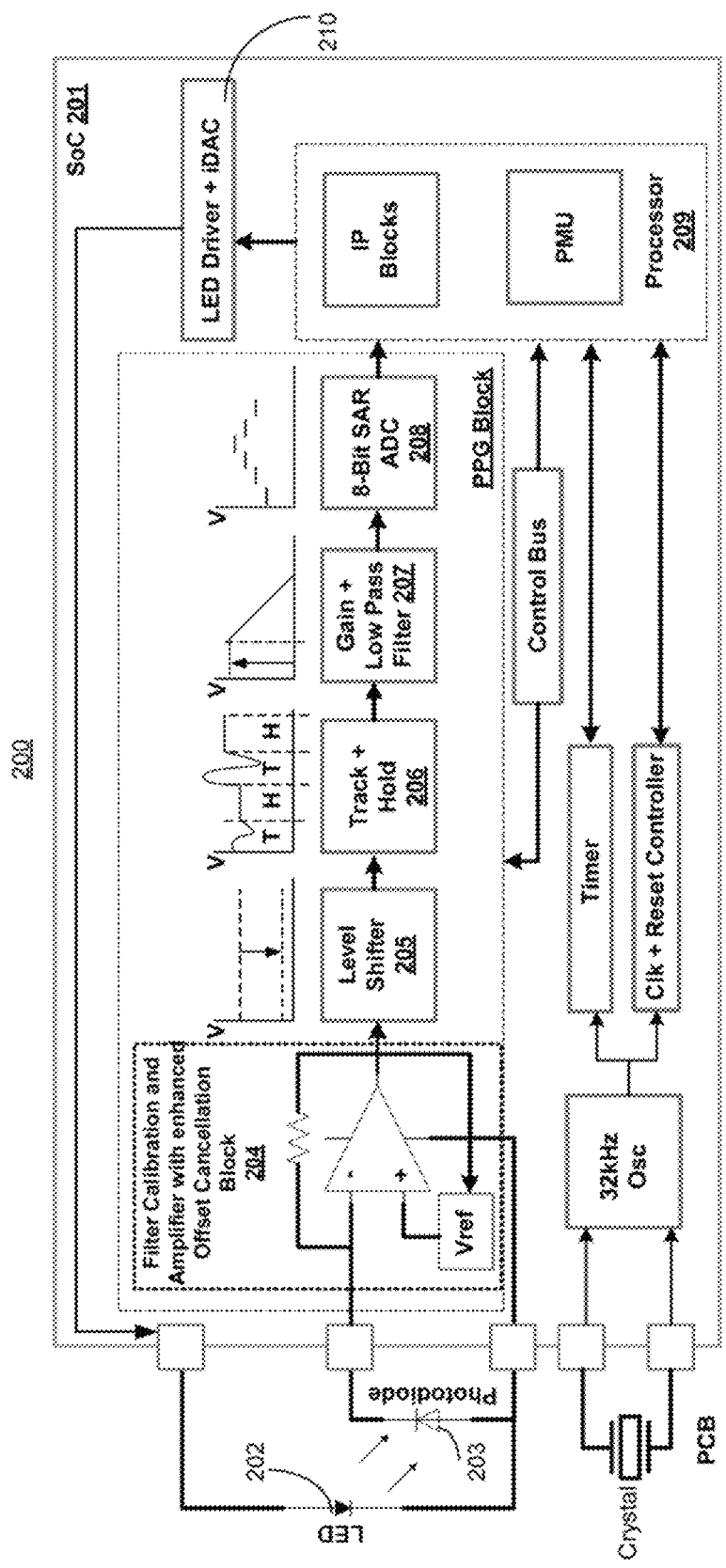
FIG. 2 illustrates a SoC (System-on-Chip) with a PPG device with apparatus to calibrate filter settling time and improve speed of tracking and cancelling of DC offset, according to some embodiments of the disclosure.

FIG. 2 illustrates apparatus 200 with a SoC (System-on-Chip) having a PPG device with apparatus to calibrate filter settling time and improve speed of tracking and cancelling of DC offset, according to some embodiments of the disclosure.

In some embodiments, apparatus 200 is part of a wearable device (e.g., a smartwatch). In some embodiments, apparatus 200 comprises SoC 201, light source (e.g., LED) 202, current-source (e.g., photodiode) 203, Filter Calibration and Amplifier with enhanced Offset Cancellation Block 204, Level Shifter 205, Track and Hold circuit 206, Amplifier (i.e., Gain stage) and Low Pass Filter (LPF) 207, Analog-to-Digital Converter (ADC) 208, Processor 209, LED Driver and current Digital-to-Analog Converter (iDAC) 210, Crystal for providing a periodic clock signal, Oscillator, Timer, Clock (Clk) and Reset Controller, and Control Bus as shown. Apparatus 200 may have fewer or more components than those listed here.

The term "light source" generally refers to a source that may provide visible light (i.e., visible to human eye and having wavelengths in the range of 400 nm to 700 nm) or invisible light (i.e., invisible to human eye and having wavelengths outside the range of 400 nm to 700 nm).

Various embodiments here are described with reference to the amplifier in Block 204 being a TIA. However, other implementations of the amplifier are also possible. Various embodiments here are described with reference to the light source being an LED. However, other implementations of the light source are also possible. Various embodiments here are described with reference to the current-source being a photodiode. However, other implementations of the current-source are also possible.

In some embodiments, current (e.g., LED current) is driven by the light source (e.g., LED driver) in response to controls provided by Processor 209. For example, the controls provided by Intellectual Property (IP) block(s), of Processor 209, for the LED driver may set the Pulse Repetition Frequency (PRF), light intensity, duty cycle ratio, and other attributes of LED 202. In some embodiments, the PRF of LED 202 is set low (e.g., several Hertz). In some embodiments, the duty cycle ratio is also set low (e.g., 100:1). For example, the off-time of LED 202 has a longer duration than the on-time of LED 202. In some embodiments, this control timing scheme of LED 202 allows to conserve power because LED 202 consumes hundreds of milli-Amperes (mA). In some embodiments, photodiode 203 is an off-chip diode which receives the light reflected off the user's wrist. In some embodiments, photodiode 203 is integrated in SoC 201 such that it is able to receive light.

In some embodiments, the current generated by photodiode 203 is received by Block 204. For example, the current corresponding to the pulsed light transmitted by LED 202 and reflected off from the organs or bones of the user's wrist is received by TIA Block 204. In some embodiments, Block 204 calibrates filter settling time and improves speed of tracking and cancelling of DC offset. In some embodiments, the calibration of settling time and improvement of speed of tracking and cancelling of the DC offset present from the received signal is performed using schemes described with reference to FIGS. 3-14.

Referring back to FIG. 2, Block 204 generates a voltage output which is level shifted down to a suitable common mode and held between pulses of LED 204 by Track and Hold Filter 206. Any suitable circuit can be used for implementing Track and Hold Filter 206. The output of Track and Hold Filter 206 are stripped-out AC waveforms (i.e., portions of the AC waveforms) as shown, according to some embodiments. In some embodiments, the output of Track and Hold Filter 206 are presented to an active second order low pass filter (i.e., Gain and Low Pass Filter 207). In some embodiments, Gain and Low Pass Filter 207 includes an amplifier to amplify the output of Track and Hold Filter 206 and to filter the high frequency AC component from the output. In some embodiments, Gain and Low Pass Filter 207 has enough gain to excite ADC 208. In some embodiments, ADC 208 is a Successive Approximation Register (SAR) based ADC.

SAR based ADC 208 is a type of ADC that converts a continuous analog waveform (i.e., filtered output of Gain and Low Pass Filter 207) into a discrete digital representation via a binary search through all possible quantization levels before finally converging upon a digital output for each conversion. In some embodiments, ADC 208 is designed such that poles are placed to limit aliasing. In some embodiments, ADC 208 is 8-bit SAR topology sampling at around 100 Hz and using around 20 dB of gain after trans-impedance of about 1.8 MegR. In other embodiments other types of ADCs may be used to digitize the filtered content from Gain and Low Pass Filter 207.

In some embodiments, ADC 208 is switched on to sample the signal presented by the chain (i.e., blocks 203, 204, 205, 206, and 207) when LED 202 is pulsed on. In some embodiments, the entire system can be shut down between LED on phases to conserve battery power. For example, when LED 202 is off, the detection mechanism having Block 204 along with other components may be turned off to conserve power. In some embodiments, the DC information required to track the signal at the next on phase is held on integrated MOS capacitors. Here, leakage may not be a major concern with this system as merely small portions of the large DC levels held may leak away, and not the signal of interest itself.

In some embodiments, Processor 209 processes the output of ADC 208 to generate a result (e.g., heartbeat, pulse rate, blood pressure, etc.). In some embodiments, Processor 209 may include Power Management Unit (PMU) to manage the power consumption of various blocks of SoC 201. In some embodiments, Processor 209 includes a plurality of Intellectual Property (IP) Blocks such as caches, memory controller, register files, input-output circuits, execution units, etc. In some embodiments, Processor 209 controls various attributes of LED 202, such as the strength of light generated by LED 202, by controlling LED Driver and current DAC (iDAC) 210.

In some embodiments, a 32 kHz oscillator (osc) is provided to illustrate the low clock frequency uses of this circuitry (and therefore low power). In some embodiments, Timer/reset controller are generic features associated with a generated clock. In some embodiments, the control bus is intended to be a digital interface between Processor 209 and the PPG Block. In some embodiments, the Control Bus can be used to trim values, control lines, and/or enables, any form of logic level information that may be passed to and from the PPG Block.

Figure 3A:
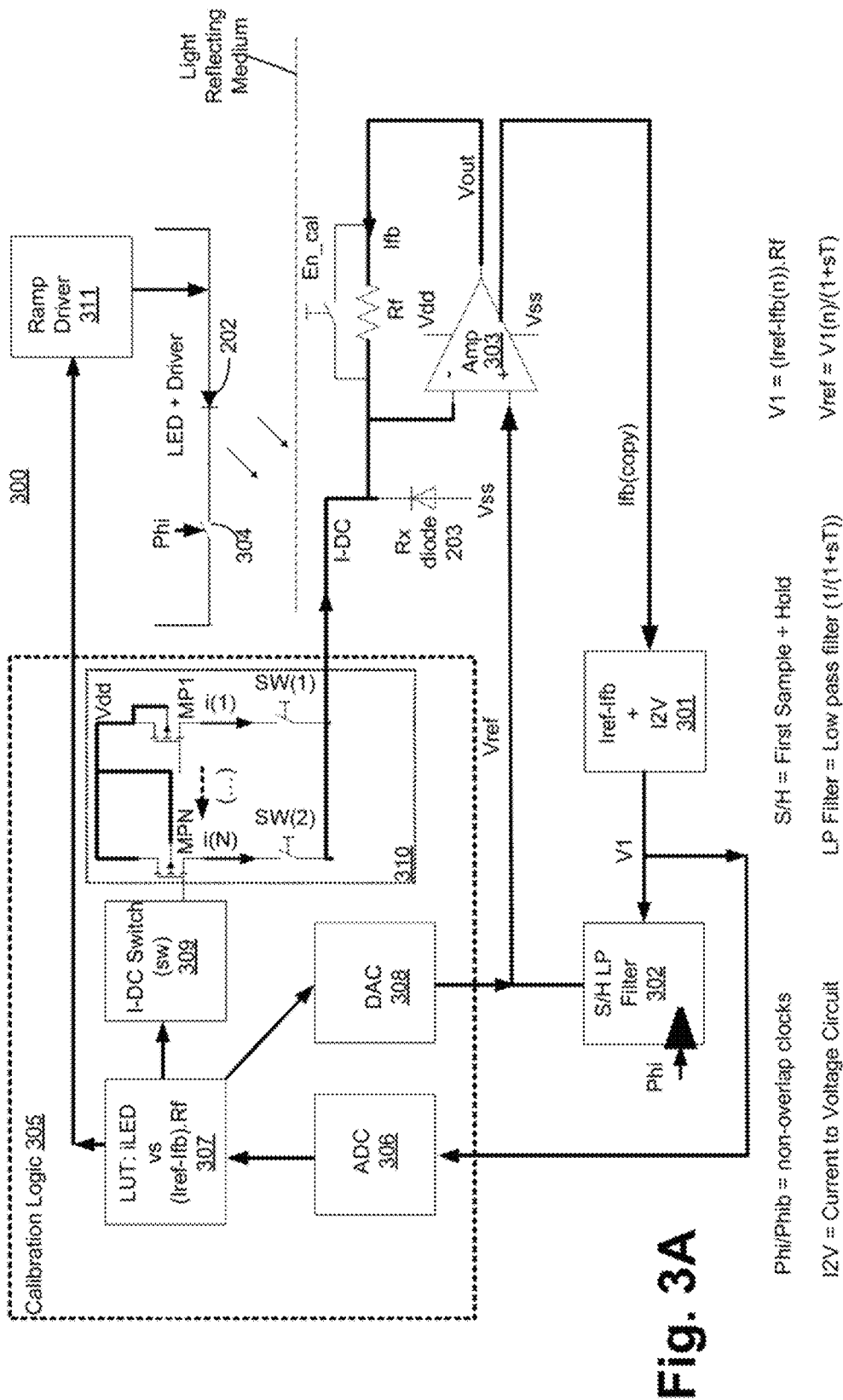
FIG. 3A illustrates a front-end of the PPG device with apparatus to calibrate filter settling time and improve speed of tracking and cancelling of DC offset, according to some embodiments of the disclosure.

FIG. 3A illustrates front-end 300 of the PPG device with apparatus to calibrate filter settling time and improve speed of tracking and cancelling of DC offset, according to some embodiments of the disclosure. It is pointed out that those elements of FIG. 3A having the same reference numbers (or names) as the elements of any other figure can operate or function in any manner similar to that described, but are not limited to such.

In some embodiments, front-end 300 comprises light source 202 (e.g., LED 202), current source 203 (e.g., photodiode 203 which is also referred to as the receiver (Rx) diode), Current-to-Voltage (I-to-V) Converter 301, Sample and Hold Low Pass Filter (S/H LP Filter) 302, amplifier 303, LED on/off switch 304, feedback resistor Rf, Calibration Logic 305, and Ramp Driver 311. In some embodiments, a compensation capacitor Cf (not shown) is added in parallel to the feedback resistor Rf. In some embodiments, a switch for enabling a calibration mode is added in parallel to the feedback resistor Rf, where the switch is controllable by En_cal (a calibration control signal). This switch is also referred to as the En_cal switch.

Various embodiments here are described with reference to amplifier 303 being a TIA (hence, TIA 303). However, other implementations of amplifier 303 are also possible. Various embodiments here are described with reference to light source 202 being an LED (hence, LED 202). However, other implementations of light source 202 are also possible. Various embodiments here are described with reference to current-source 203 being a photodiode (hence, photodiode 203). However, other implementations of current-source 203 are also possible.

In some embodiments, pulsed current generated by photodiode 203 is received by TIA 303 and a copy (i.e., copy of Ifb) of it is provided to I-to-V (I2V) Converter 301 (also illustrated by its function Iref-Ifb and I2V). In some embodiments, the current generated by photodiode 203 is pulsed by switch 304 which is controlled by control signal Phi. In some embodiments, when Phi is logic high (e.g., a first phase or a high phase), switch 304 is closed allowing LED 202 to shine light on the light reflecting medium (e.g., wrist of a user). In some embodiments, when Phi is logic low (e.g., second phase or low phase), switch 304 is off which causes LED 202 to be off. In some embodiments, both Phi and Phib signals are non-overlapping clocks.

In some embodiments, I-to-V Converter 301 receives a copy of the photodiode current and converts that current to a corresponding voltage V1. Here, the labels for nodes and signals are interchangeably used. For example, V1 may refer to node V1 or voltage V1 on that node. In some embodiments, by converting the current to V1, the current is sampled from photodiode 203 and used for feed-forward DC offset cancellation at the input stage of TIA 303. In some embodiments, the output voltage V1 from I-to-V Converter 301 is scaled to a proportional-to-Rf voltage, where Rf is a resistance which is the same as the resistance of feedback resistor Rf of TIA 303. In some embodiments, the output voltage V1 from I-to-V Converter 301 is proportional to the input photodiode current. The output voltage has an AC component (which is the desirable signal) and a DC component (which may be the undesirable signal).

In some embodiments, the output voltage V1 (i.e., the output of I-to-V Converter 301) is sampled and then held by S/H LP Filter 302. In some embodiments, S/H LP Filter 302 removes the AC component and stores the DC component in a capacitive device (e.g., a MOS based capacitor or any other type of capacitor). In some embodiments, the low pass filter of S/H LP Filter 302 filters the AC component (of the output voltage from I-to-V Converter 301) using a switched capacitor and a resistor leaving the DC component. In some embodiments, a MOS based capacitor or any other type of capacitor coupled in series with a switch is used to implement the switched capacitor. In some embodiments, the resistor of the S/H LP Filter 302 is a MOS based resistance (i.e., a transistor operating in the linear region).

In some embodiments, the output voltage V1 is sampled when Phi is logic high (i.e., when LED 202 is on). In some embodiments, the output DC component of S/H LP Filter 302 is an output voltage Vref which is to function as a reference voltage for TIA 303. In some embodiments, I-to-V Converter 301 causes the output voltage (i.e., the DC component held by S/H LP Filter 302) to lower in voltage level as the DC component of the input current increases (i.e., as the current generated by photodiode 203 increases).

In some embodiments, TIA 303 has an inverting input and a non-inverting input. In some embodiments, a voltage is applied to the non-inverting input while the inverting input is set by a current sum to zero via resistor Rf and photodiode 203 paths. In some embodiments, during normal DC offset cancelling mode, the output Vref of S/H LP Filter 302 is provided to the non-inverting input of the input stage of TIA 303 in order to bring its output back down to the desired common mode level. In some embodiments, during a calibration mode, S/H LP Filter 302 is disabled or its output is tri-stated and Vref is provided by Calibration Logic 305.

TIA 303 is a current-to-voltage converter that converts current from photodiode 203 to an output voltage Vout relative to a reference voltage Vref. The gain of TIA 303 depends on the feedback resistor having resistance Rf. In some embodiments, TIA 303 is implemented as an operational amplifier. One reason for using TIA 303 with photodiode 203 is that photodiode 203 has a current response which is more linear than a voltage response. In some embodiments, TIA 303 presents a low impedance to photodiode 203 and isolates it from the output voltage Vout of TIA 303 via resistor Rf. In some embodiments, a compensation capacitor Cf (not shown) is added in parallel to resistor Rf to provide stability to the feedback loop from the output of TIA 303 to its inverting input.

In some embodiments, photodiode current is simultaneously sensed in a separate parallel path (through the inverting input of TIA 303). In some embodiments, a copy of the photodiode current seen in feedback resistor Rf is provided by a dual output stage amplifier 303, and this duplicate photodiode current is then subtracted from a reference current and the resultant current is then pushed through a duplicate resistor Rf (shown in FIGS. 12-14).

Referring back to FIG. 3A, in some embodiments, the output voltage of I-to-V Converter 301 is level shifted up and buffered by a transistor (e.g., a p-type transistor). In some embodiments, the buffered voltage is filtered with a large time constant using an on-die capacitor and a resistor and fed forward to the non-inverting input of TIA 303. In some embodiments, the on-die capacitor and the resistor are part of the S/H LP Filter 302.

In some embodiments, because the DC current was subtracted from a reference and then undergone the same impedance conversion as Vout through resistor Rf, the DC level at the non-inverting input of TIA 303 is brought down. As such, the DC level at the output of TIA 303 is lowered, and the offset is cancelled. In some embodiments, if the feedforward frequency pole is suitably low, the AC component passes through TIA 303.

In some embodiments, Calibration logic 305 comprises an ADC 306, LUT 307, and DAC 308. In some embodiments, Calibration logic 305 is an enhanced calibration logic which includes (in addition to ADC 306, LUT 307, and DAC 308) I-DC Switch (sw) 309, and a circuit 310 having a plurality of transistors with corresponding switches to provide I-DC current injection to Rx diode 203.

In some embodiments, Calibration logic 305 is operable to map a transfer function for subsequent initialization of S/H LP Filter 302. In some embodiments, Calibration logic 305 is operable to exploit the control over LED drive current and the received current (from the photodiode) to map transfer function of the reflective medium (i.e., current in and current/voltage out). In some embodiments, Calibration logic 305 is operable to use this information (i.e., the transfer function) to digitally hold predicted photo currents in LUT 307. In some embodiments, Calibration logic 305 is operable to apply information in LUT 307 to an offset cancelling frontend to initialize S/H LP Filter 302 to hold the correct DC value (i.e., Vref) for the selected LED current.

In some embodiments, during calibration mode, TIA 303 is configured as a unity gain stage by shorting the resistor Rf (e.g., via En_Cal signal that can cause the resistor Rf to short by closing a switch). During this calibration mode, I-DC path is disconnected from reaching Rx diode 203, in accordance with some embodiments. In some embodiments, I-to-V Converter 301 rapidly conveys the photodiode current (e.g., copy of the photodiode current) as output voltage V1. In some embodiments, during calibration mode, S/H LP Filter 302 is disabled or its output is tri-stated and Vref is provided by Calibration Logic 305. In some embodiments, ADC 306 converts the voltage V1 to a digital representation.

Any suitable ADC may be used to implement ADC 306. For example, ADC 306 is one of: direct-conversion ADC (for flash ADC), two-step flash ADC, successive-approximation ADC (SAR ADC), ramp-compare ADC, Wilkinson ADC, integrating ADC, delta-encoded ADC or counter-ramp, pipeline ADC (also called subranging quantizer), sigma-delta ADC (also known as a delta-sigma ADC), time-interleaved ADC, ADC with intermediate FM stage, or time-stretch ADC. For purposes of explaining the various embodiments, ADC 306 is considered to be flash ADC.

In some embodiments, this digital representation from ADC 306 is stored in LUT 307. In some embodiments, this digital representation from ADC 306 is processed before being stored in LUT 307. For example, the digital representation from ADC 306 is scaled, compressed, or encoded before being stored in LUT 307. In some embodiments, LUT 307 maps the digital representation of V1 with photodiode current. In some embodiments, LUT 307 is populated with a plurality of photodiode current levels and corresponding digital representation of V1 associated with the current levels. In some embodiments, LUT 307 is powered by an always-on power supply. In some embodiments, LUT 307 is a non-volatile memory (NVM) such as NAND flash memory or magnetic random access memory (RAM). In other embodiments, other types of memories or registers may be used to implement LUT 307.

In some embodiments, Ramp Driver 311 (or ramp generator) ramps the drive current to LED 202. For example, Ramp Driver 311 ramps up (i.e., increments) the drive current by a predetermined or programmable current step and then the corresponding digital representation of V1 associated with the photodiode current is stored in LUT 307. In another example, Ramp Driver 311 ramps down (i.e., decrements) the drive current by a predetermined or programmable current step and then the corresponding digital representation of V1 associated with the photodiode current is stored in LUT 307.

In some embodiments, digital-to-analog converter (DAC) 308 drives the appropriate DC value for Vref, during calibration mode (i.e., when S/H LP Filter 302 is disabled), using the data stored in LUT 307. In some embodiments, based on the stored V1 value in LUT 307, the Vref may be adjusted to center the value to maximize the dynamic range of TIA 303 so that the optimum value of Vref is selected based on the current set in LED 202 to avoid clipping as the current is increased or decreased.

In some embodiments, DAC 308 is pulse width modulation DAC. In other embodiments, other types of DAC may be used for implementing DAC 308. For example, interpolating DAC (also known as oversampling DAC), binary weighted DACs (e.g., switched resistor DAC, switched capacitor DAC, switched current-source DAC), R-2R ladder DAC, thermometer coded DAC, segmented DAC, etc. may be used for implementing DAC 308. Any suitable DAC may be used for implementing DAC 308.

As such, Calibration logic 305 exploits control over LED current (via Ramp Driver 311) and the received photodiode current to map the transfer function of reflective medium (current in and current/voltage out) and uses this information to digitally hold predicted photo currents in LUT 307. In some embodiments, Calibration logic 305 applies the analog version of digital representation stored in LUT 307 to an offset cancelling frontend to initialize S/H LP Filter 302 to hold the correct DC value for the selected LED current.

Figure 4:
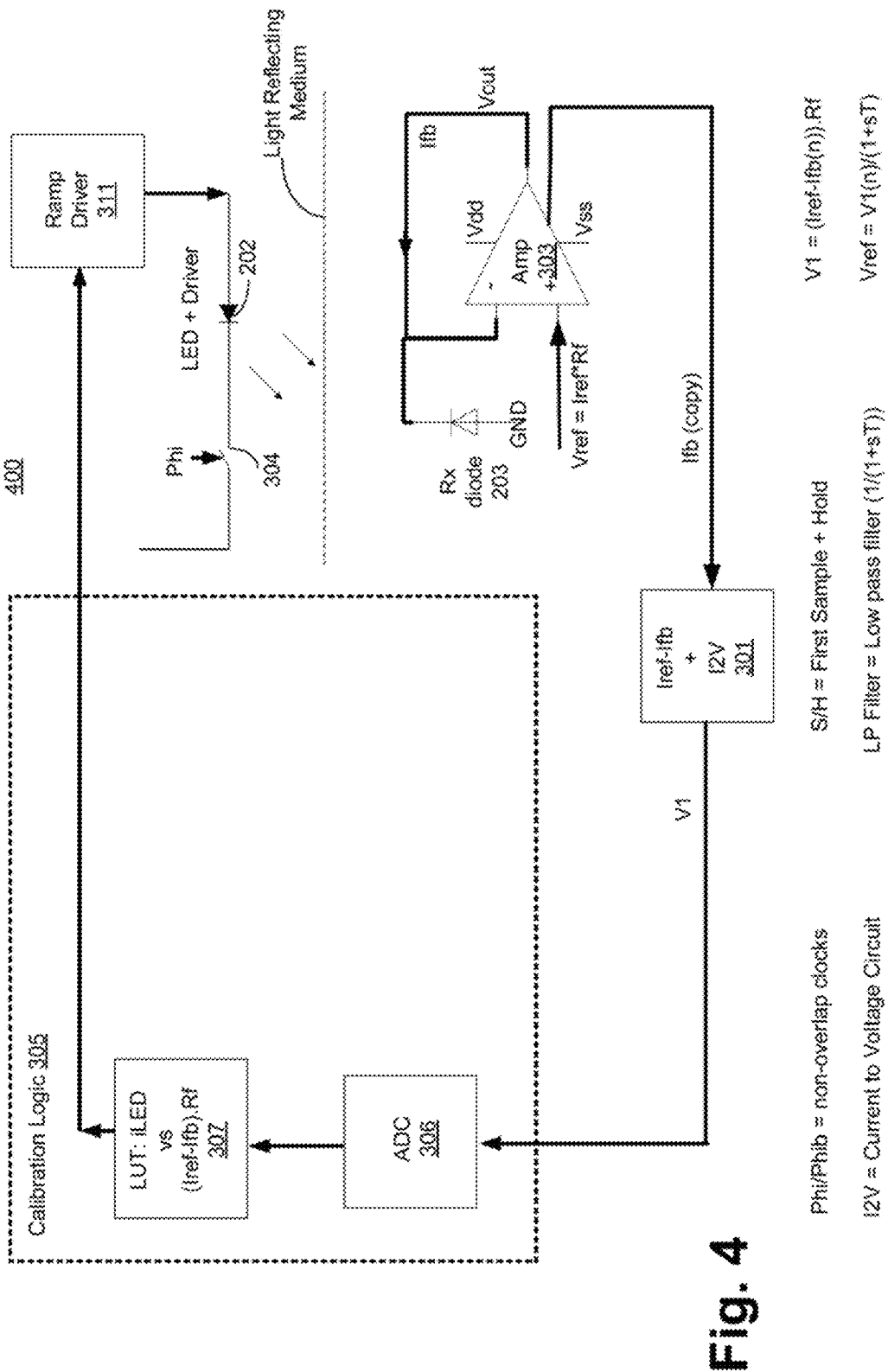
FIGS. 4-6 illustrate the front-end of the PPG device at different stages of calibrating the filter settling time and improving speed of tracking and cancelling of DC offset, according to some embodiments of the disclosure.
Figure 5:
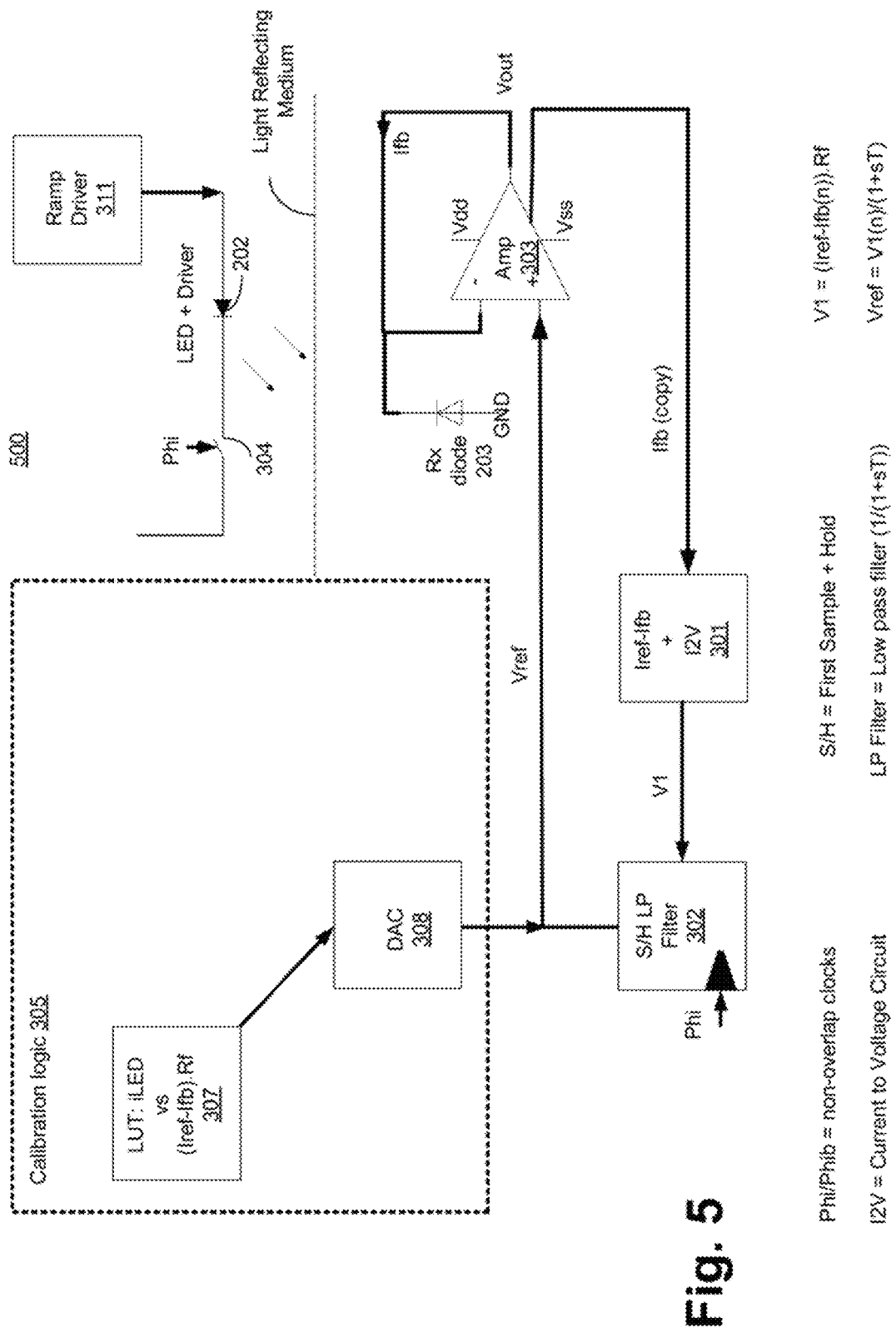
Figure 6:
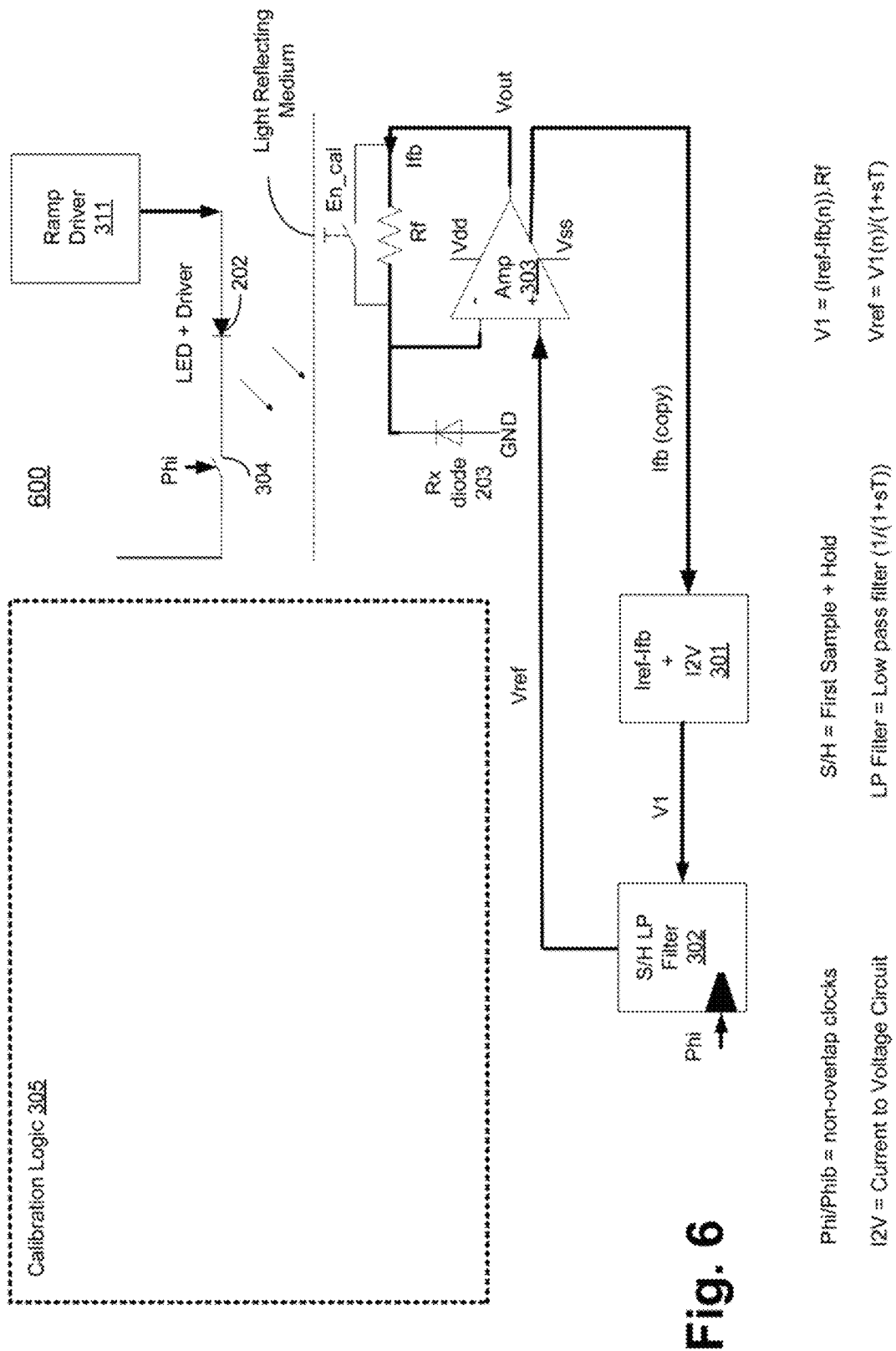

After Vref is initialized by the output of DAC 308, in some embodiments, DAC 308 is disabled, resistor Rf is unshorted (i.e., enabled back into the feedback loop), and the offset cancelation process performs normally. By initializing Vref to the estimated DC component level during calibration mode, the process of DC offset cancellation is accelerated during normal operation mode. FIGS. 4-6 illustrates the front-end of the PPG device at different stages of calibrating the filter settling time and for improving speed of tracking and cancelling of DC offset, according to some embodiments of the disclosure.

Referring back to FIG. 3A, in some embodiments, Calibration logic 305 is an enhanced calibration logic which includes (in addition to ADC 306, LUT 307, and DAC 308) I-DC Switch (sw) 309, and a circuit 310 having a plurality of transistors with corresponding switches to provide I-DC current injection to Rx diode 203. In some embodiments, I-DC switch 309 is controlled (via a state machine which is not shown here) to provide coarse DC currents (I-DC) to linearize Vref.

In some embodiments, the enhanced calibration logic of Calibration logic 305 monitors for clipping of voltage V1. To achieve higher Signal-to-Noise Ratio (SNR), the gain of TIA 303 is made as large as possible, in accordance with some embodiments. However, as the gain of TIA 303 is made large, V1 may clip. For example, V1 may collapse (or clip) to ground. In another example, when voltage V1 reaches power supply rail levels (e.g., Vdd or near Vdd) or ground level (e.g., Vss or near Vss), V1 is considered to be clipping. When V1 clips, the feedback loop (i.e., electrical loop from TIA 303, I-to-V Converter 301, S/H LP Filter 302, and back to TIA 303) does not operate properly. To mitigate the effect of clipping, I_DC current is injected by Calibration Logic 305 into the resistor Rf path to bring the voltage level of V1 away from the clipping zone (e.g., Vss or near Vss).

As such, in some embodiments, Calibration Logic 305 injects a coarse DC current straight to photodiode 203 during transfer function mapping. In some embodiments, this current is injected when clipping on voltage V1 due to too large a photocurrent, as seen by the digital codes from ADC 306, is received (in this case clipping is when $I_{photodiode} > I_{ref}$). The coarse DC current I_DC can be added either incrementally and/or SAR style to re-center the V1 readings, in accordance with some embodiments.

Figure 7:
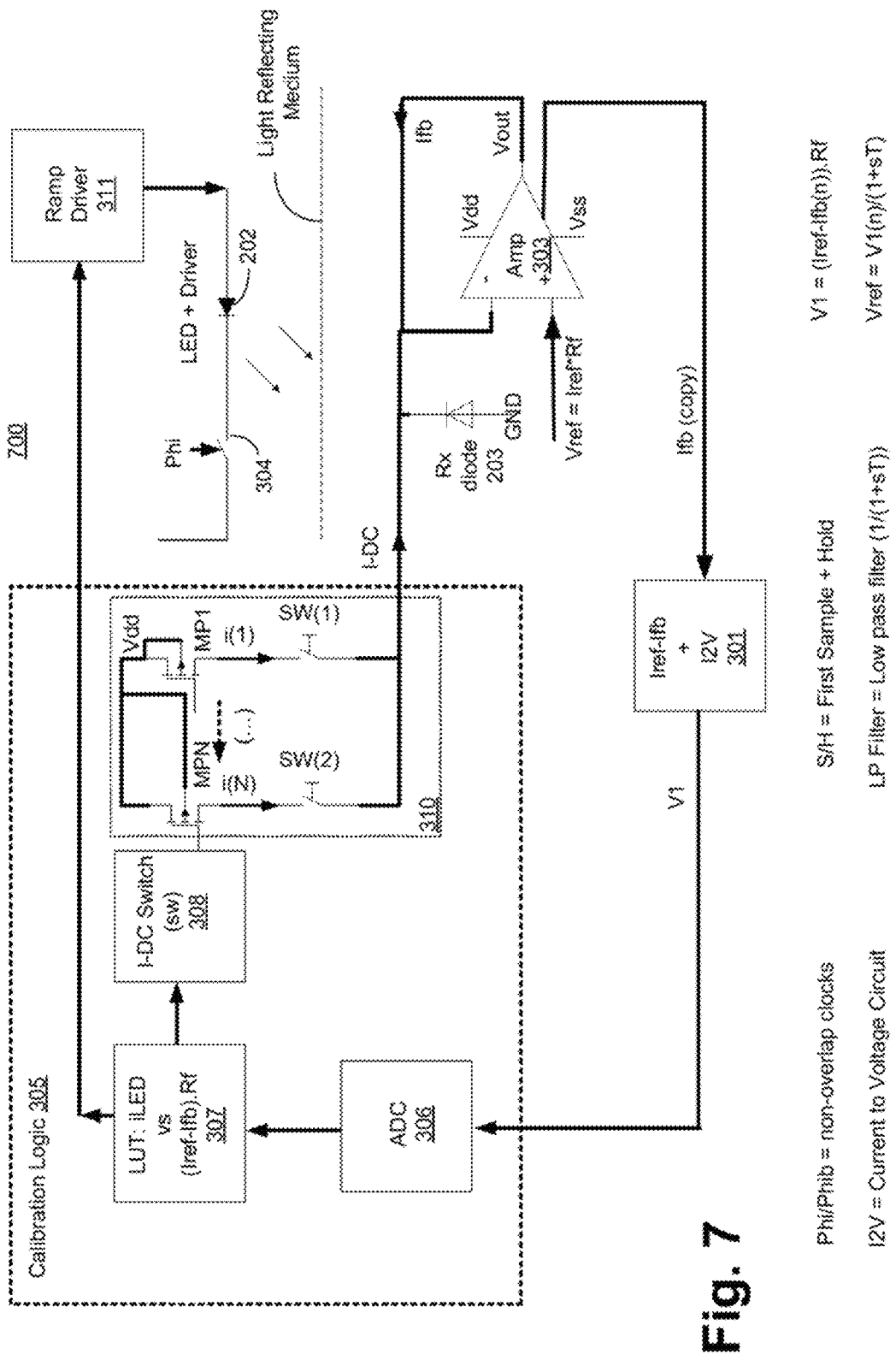
FIGS. 7-9 illustrate the front-end of the PPG device at different stages of calibrating the filter settling time and improving speed of tracking and cancelling of DC offset, according to some other embodiments of the disclosure.
Figure 8:
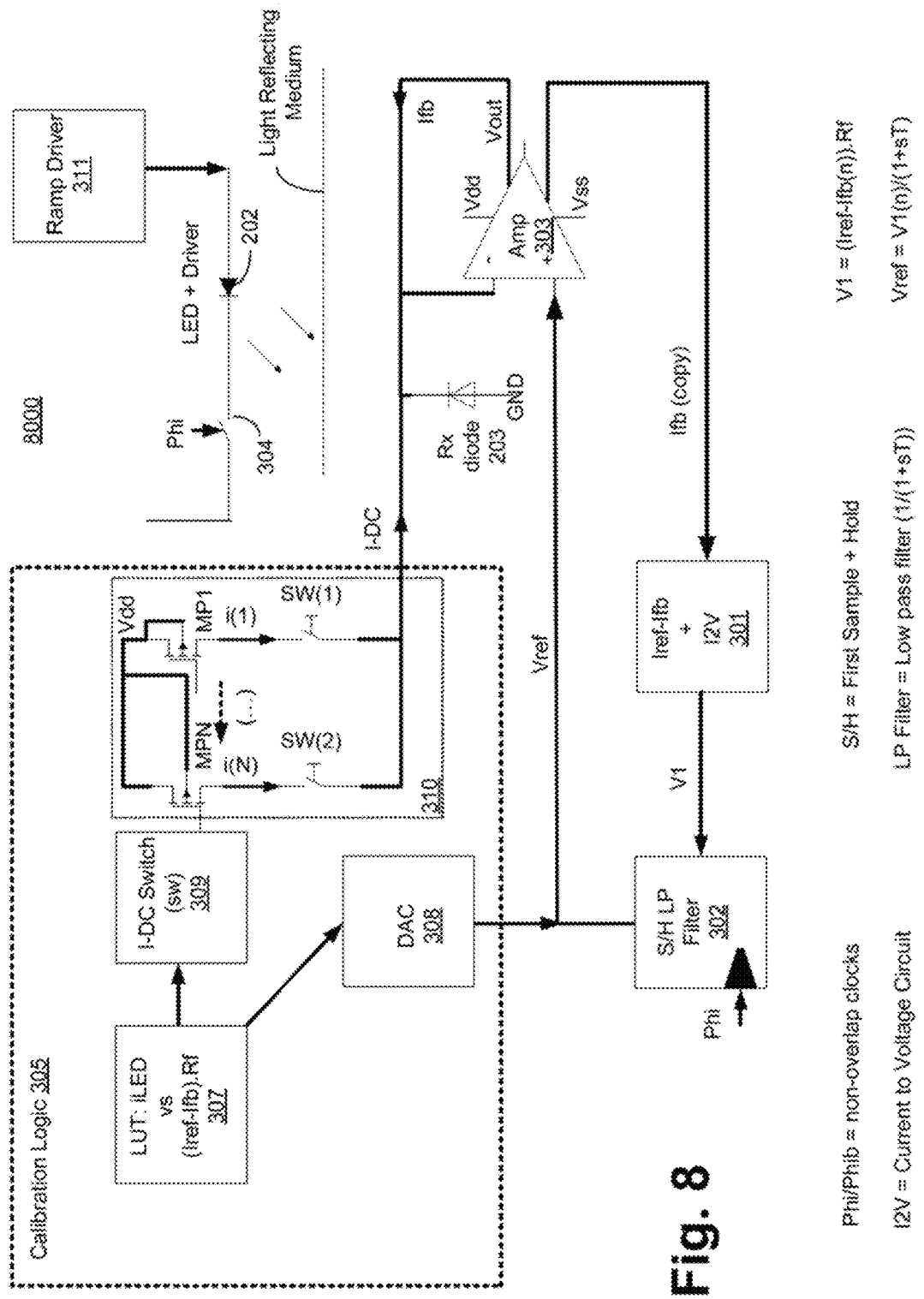
Figure 9:
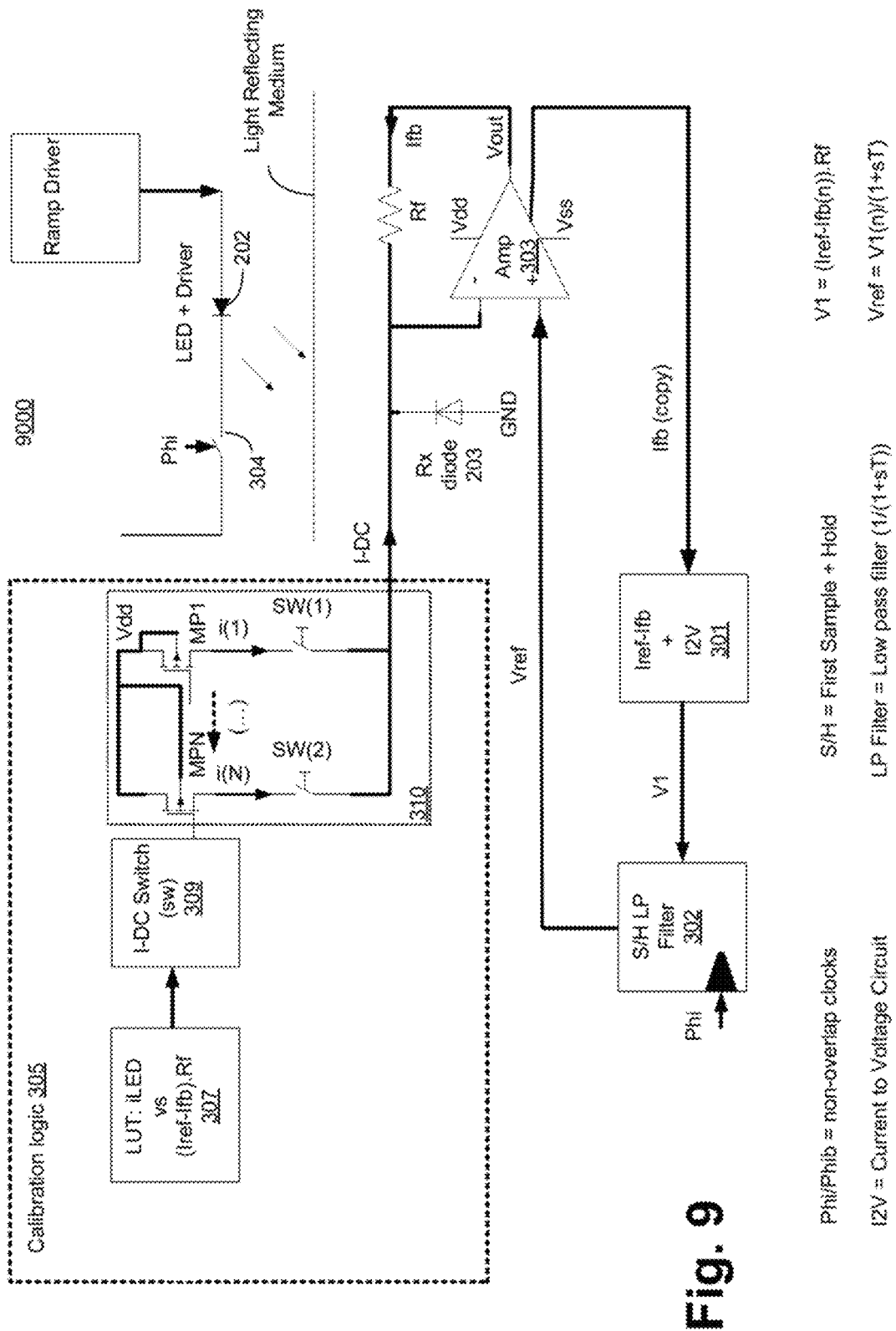

With the enhanced calibration logic, in some embodiments, the transfer function mapping table shows both the filter voltage (to set for enhanced acquisition speed) and also the DC current to inject to avoid clipping (enhance gain and/or offset handling) for every LED current chosen. With the enhanced calibration logic, resistance of resistor Rf can be made much larger in design to give more transimpedance gain. A higher transimpedance gain translates to better SNR. Also the linear range of the offset correction circuitry can be many times larger as not all current will need to flow back through Rf. FIGS. 7-9 illustrate the front-end of the PPG device at different stages of calibrating the filter settling time and improving speed of tracking and cancelling of DC offset using the enhanced calibration logic, according to some other embodiments of the disclosure.

Referring back to FIG. 3A, in some embodiments, the switch for enabling calibration (En_Cal) allows the calibration to be performed quicker as a frequency pole is removed in the TIA feedback loop (Rf/Cdiode, where Cdiode is the capacitance of photodiode 203). With Calibration Logic 305 enabled, calibration can complete in milliseconds, as opposed to natural (less than 0.5 Hz) filter settling time, which may take seconds. In some embodiments, the switch controlled by En_Cal makes TIA 303 behave as a unity gain buffer which attempts to provide a current to balance that conducted by photodiode 203 and equalize the inverting input to the non-inverting input (which is fixed at Iref*Rf during calibration mode).

In some embodiments, the photodiode current (e.g., taken as a copy from the output of TIA 303) is used during calibration to drive I-to-V Converter 301 to ensure that the signal read by ADC 306 is scaled in exactly the same way as the DC correction loop would scale it. The difference is that ADC 306 is connected to the I-to-V Converter 301 output before it is filtered (i.e., S/H LP Filter 302 can be held in a reset state during calibration).

In some embodiments, LED drive current is swept (i.e., ramped up or down) giving a sweep in light intensity which is received as a current by photodiode 203. In some embodiments, this photodiode current is subtracted from a reference current (Iref) and then converted to a sweeping voltage at the output of I-to-V Converter 301 through a resistor Rf which is equal in resistance to resistor Rf coupled in feedback with TIA 303. In some embodiments, this voltage V1 is then converted by ADC 306 and digitally stored in LUT 307 to allow mapping of LED drive current to DC offset at the filter output. Simultaneously, in some embodiments, the ADC codes can be monitored for clipping of the voltage V1 and a static DC offset current is selected and injected into photodiode 203 through I-DC to linearize the Vref transfer function for larger received currents.

Figure 3B:
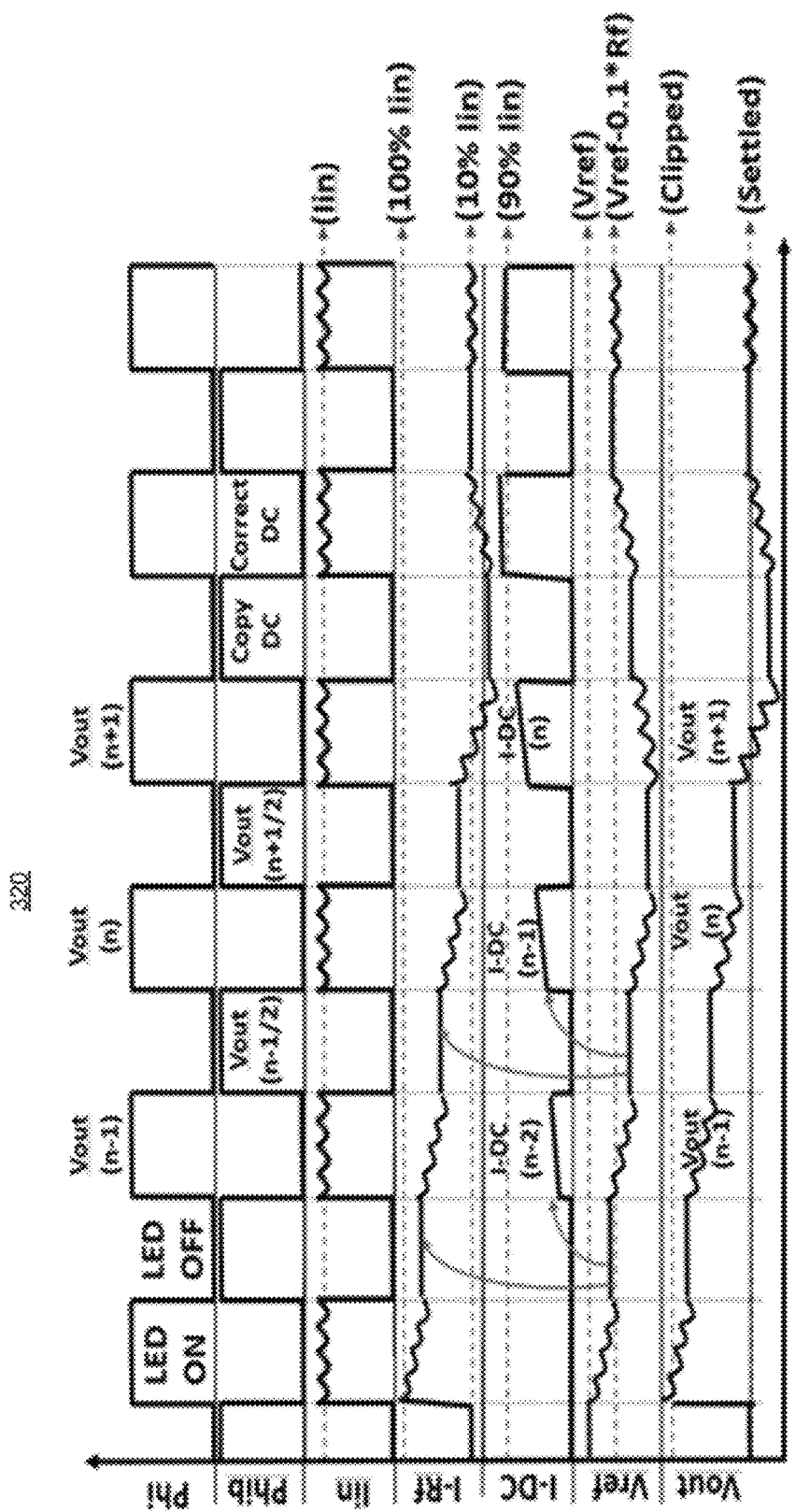
FIG. 3B illustrates a plot showing the offset cancellation process, according to some embodiments of the disclosure.

FIG. 3B illustrates plot 320 showing the offset cancellation process, according to some embodiments of the disclosure. It is pointed out that those elements of FIG. 3B having the same reference numbers (or names) as the elements of any other figure can operate or function in any manner similar to that described, but are not limited to such. Here, x-axis is time and y-axis is voltage or current depending on the waveform.

FIG. 3B is a graphical representation of the DC cancellation process when the apparatus of FIG. 3A receives a typical PPG signal. The waveforms from the top are non-overlapping clocks Phi and Phib, photodiode current (Iin), current through resistor Rf (I-Rf), DC current injected by Calibration Logic 305 (I-DC), reference voltage (Vref) received at the non-inverting input of TIA 303, and output (Vout) of TIA 303. The waveforms show that as I-DC current is injected, clipping is mitigated, and Vref and Vout voltages settle such that DC offset is cancelled.

In some embodiments, S/H LP Filter 302 involved in removing the DC is synthesised using high density MOS capacitors and either a switched capacitor or Ohmic region MOS configuration to provide a large resistance. S/H LP Filter 302 is predictably slow to settle. In some embodiments, settling time for S/H LP Filter 302 is overcome by exploiting the control over the LED current (also referred to as the drive current) and the available access to the un-filtered reference voltage at the non-inverting input of TIA 303.

In some embodiments, by using ADC 306, a complete DC transfer function of LED current vs required S/H LP Filter 302 voltage V1 can be obtained. In some embodiments, this transfer function is achieved by a rapid staircase in LED current with an ADC sample at each step (by ADC 306), and digitizing the result in LUT 307. By driving DAC 308, this LUT calibration can initiate the filter to begin unclipped signal acquisition in just milliseconds, in accordance with some embodiments.

In some embodiments, the calibration can be re-performed at any time during use if the output of ADC 306 appears clipped (e.g., all bits are zeros or ones). In some embodiments, the contents of LUT 307 can determine if the reference current level (Iref) is being exceeded at the peak LED current in-application. When this occurs, a DC current (I-DC) of appropriate magnitude is driven directly into photodiode 203 to re-centre the reference voltage Vref on the non-inverting TIA input, in accordance with some embodiments. By adding this feature, large TIA gains approaching 10 MegR can be achieved in the presence of offsets in the order of many microamperes.

FIGS. 4-6 illustrate the front-end of the PPG device at different stages 400, 500, and 600 of calibrating the filter settling time and improving speed of tracking and cancelling of DC offset, according to some embodiments of the disclosure. It is pointed out that those elements of FIGS. 4-6 having the same reference numbers (or names) as the elements of any other figure can operate or function in any manner similar to that described, but are not limited to such.

In some embodiments, as illustrated by the configuration of frontend during calibration stage 400, TIA 303 is configured as a unity gain buffer by shorting resistor Rf via En_Cal signal. During calibration stage 400, S/H LP Filter 302 is disabled (which is why it is removed from FIG. 4). In some embodiments, for each LED drive current (which is set by Ramp Driver 311), Calibration Logic 305 converts the voltage V1 to a digital representation and stores the LED drive current setting and corresponding voltage V1 in LUT 307. As such, LUT 307 is populated with a wide range of LED drive current and corresponding voltage V1.

In some embodiments, as illustrated by the configuration of frontend during calibration stage 500, DAC 308 is enabled while S/H LP Filter 302 remains disabled. In some embodiments, calibration stage 500 follows calibration stage 400. In some embodiments, a state machine (not shown) selects a row (or a portion) of LUT 307 with a digital representation of V1 that corresponds the DC component observed in photocurrent from Rx diode 203. In some embodiments, this digital representation is provided to DAC 308 which generates a corresponding analog voltage. In some embodiments, this analog voltage is provided as initial Vref to the non-inverting input of TIA 303.

In some embodiments, as illustrated by the configuration of frontend during calibration stage 600, DAC 308 is disabled while S/H LP Filter 302 is enabled. During calibration stage 600, En_Cal causes the switch to open (i.e., resistor Rf is no longer shorted). As such, TIA 303 now operates in normal mode as a transimpedance amplifier. In some embodiments, calibration stage 600 follows calibration stage 500. Since Vref was initialized by DAC 308 to an estimated DC component level, Vref now begins to settle to a stable level quickly by the feedback loop (i.e., loop formed by TIA 303, I-to-V Converter 301, and S/H LP Filter 302).

FIGS. 7-9 illustrate the front-end of the PPG device at different stages 700, 800, and 900 of calibrating the filter settling time and improving speed of tracking and cancelling of DC offset, according to some other embodiments of the disclosure. It is pointed out that those elements of FIGS. 7-9 having the same reference numbers (or names) as the elements of any other figure can operate or function in any manner similar to that described, but are not limited to such. Calibration Logic 305 for FIGS. 7-9 is the enhanced calibration logic, in accordance with some embodiments. In some embodiments, the enhanced calibration logic is used to mitigate the effect of clipping.

In some embodiments, as illustrated by the configuration of frontend during calibration stage 700, TIA 303 is configured as a unity gain buffer by shorting resistor Rf via En_Cal signal. During calibration stage 700, S/H LP Filter 302 is disabled (which is why it is not shown in FIG. 7). The enhanced calibration logic generates a coarse DC current which is injected straight to photodiode 203 during transfer function mapping, in accordance with some embodiments. Here, coarse DC current generally refers to a step by step injection of DC current into the Rx diode 203, where the size of the step is large (hence, a coarse step) enough to noticeably reduce clipping on voltage V1.

In some embodiments, the DC current (i.e., I_DC) is injected when clipping on V1 due to too large a photocurrent is seen by the output digital codes of ADC 306. In some embodiments, the course DC current can be added either incrementally and/or SAR style to re-center the readings of voltage V1. In some embodiments, I-DC switch 309 increases I-DC current for a calibration iteration by turning on the switch associated with the transistor providing the DC current. For example, I-DC Switch 309 turns on SW(1) and so I-DC is provided by transistor MP1. In the next calibration iteration, I-DC Switch 309 may turn on SW(2) and so I-DC is provided by transistor MP2, and so on.

In some embodiments, the output of I-DC Switch 309 is binary coded, and transistors MP1-MPN are binary weighted in size to provide binary weighted I-DC current. As such, coarse I-DC is provided by Calibration Logic 305. In some embodiments, fine I-DC current may be provided. In one such embodiment, the output of I-DC Switch 309 is thermometer coded, and transistors MP1-MPN (where 'N' is an integer) are equal in size to provide thermometer weighted current for I-DC.

In some embodiments, LUT 307 for enhanced calibration is an expanded version of LUT 307 as described with reference to FIGS. 4-6. In some embodiments, LUT 307 for enhanced calibration includes the digital representation of V1, corresponding LED drive current, and I_DC current injected by Calibration logic 305. In some embodiments, for each LED drive current (which is set by Ramp Driver 311), Calibration Logic 305 converts the voltage V1 to a digital representation and stores the LED drive current setting, corresponding voltage V1, and I_DC in LUT 307. As such, LUT 307 is populated with a wide range of LED drive current, corresponding voltage V1, and I_DC values. The transfer function mapping LUT 307 shows both the filter voltage (to set for enhanced acquisition speed) and also the DC current to inject to avoid clipping (enhance gain and/or offset handling) for every LED current chosen, in accordance with some embodiments.

In some embodiments, as illustrated by the configuration of frontend during calibration stage 800, DAC 308 is enabled while S/H LP Filter 302 remains disabled. In some embodiments, calibration stage 800 follows calibration stage 700. In some embodiments, a state machine (not shown) selects a row (or a portion) of LUT 307 with a digital representation of V1 that corresponds to the DC component observed in photocurrent from Rx diode 203, and which does not show clipping on voltage V1. In some embodiments, this digital representation is provided to DAC 308 which generates a corresponding analog voltage. In some embodiments, this analog voltage is provided as initial Vref to the non-inverting input of TIA 303. In this embodiment, I-DC (according to the selected row from LUT 307) is also provided to Rx-diode 203 to ensure no clipping on voltage V1.

In some embodiments, as illustrated by the configuration of frontend during calibration stage 900, DAC 308 is disabled while S/H LP Filter 302 is enabled. In some embodiments, calibration stage 900 follows calibration stage 800. In this embodiment, Calibration Logic 305 continues to provide I-DC to photodiode 203 so voltage on V1 does not clip. This allows the frontend to operate with high gain settings (i.e., gain of TIA 303 can be made large to achieve better SNR). During calibration stage 900, En_Cal causes the switch to open (i.e., resistor Rf is no longer shorted). As such, TIA 303 now operates in normal mode as a transimpedance amplifier. Since Vref was initialized by DAC 308 to an estimated DC component level, Vref now begins to settle to a stable level quickly by the feedback loop (i.e., loop formed by TIA 303, I-to-V Converter 301, and S/H LP Filter 302).

Figure 10A:
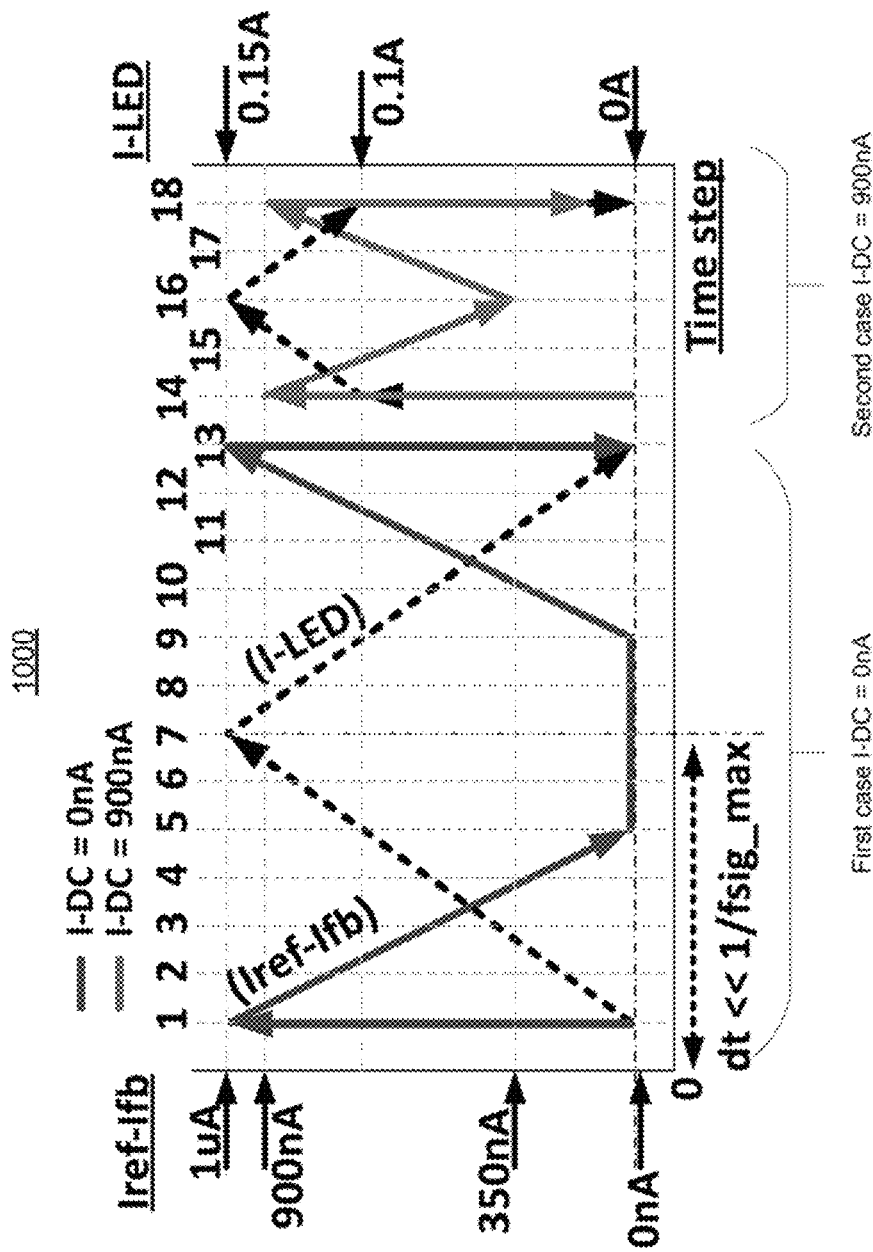
FIG. 10A illustrates a plot showing eighteen steps of a calibration example using the apparatus according to some embodiments.
Figure 10B:
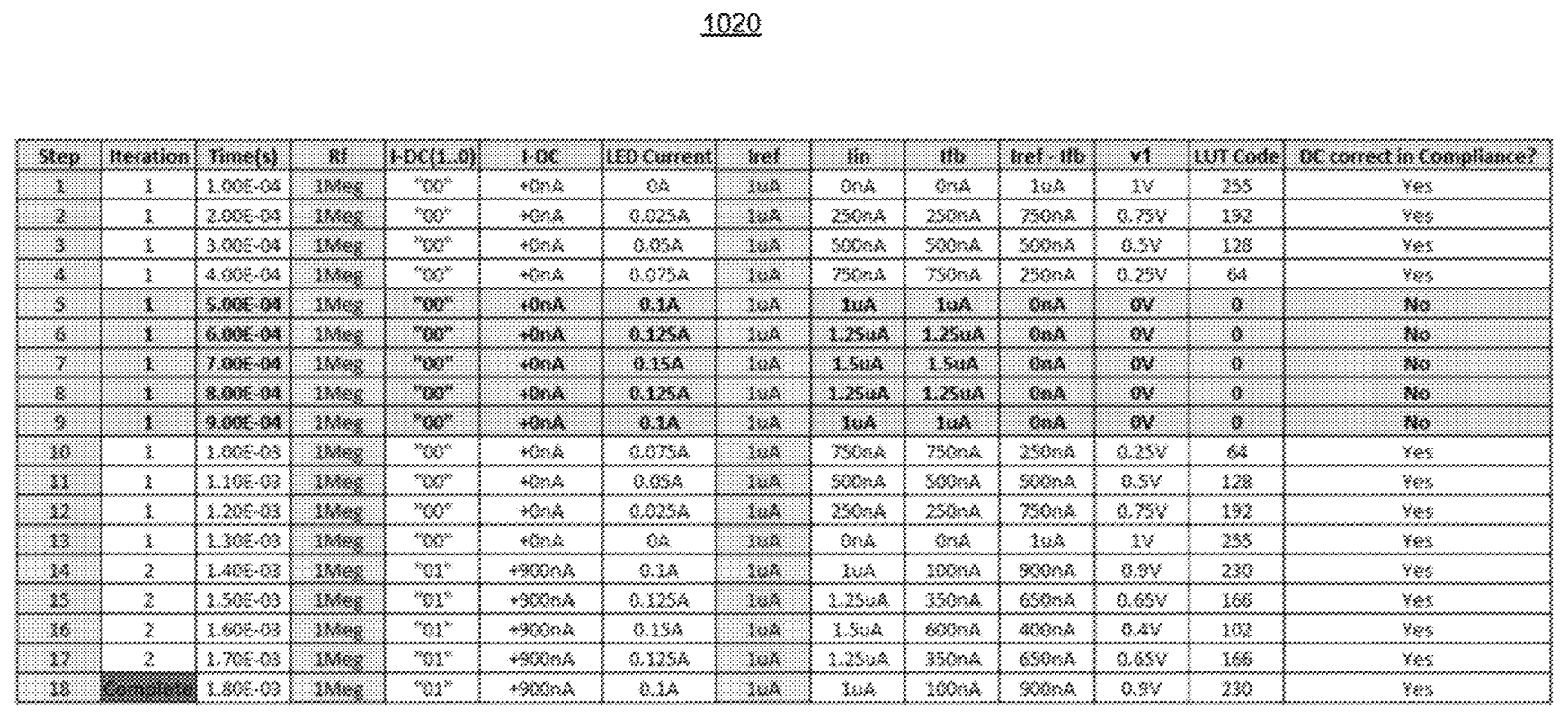

FIG. 10A illustrates plot 1000 showing eighteen steps of a calibration example using the apparatus according to some embodiments. It is pointed out that those elements of FIG. 10A having the same reference numbers (or names) as the elements of any other figure can operate or function in any manner similar to that described, but are not limited to such. Here, x-axis are eighteen time steps (1 through 18), y-axis on the right side is LED drive current (i.e., I-LED ranging from 0 A to 0.15 A), and y-axis is a difference between Iref (i.e., reference current in I-to-V Converter 301) and Ifb (i.e., copy of photodiode current), where the difference ranges from 0 nA to 1 µA. FIG. 10B illustrates table 1020 corresponding to plot 1000.

Plot 1000 shows two cases. In the first case, I-DC is 0 nA. In the second case, I-DC is 900 nA. In this example, steps 1 through 12 in LED current are traversed for the first case (i.e., LED current of 0-150 mA up and down). In some cases, ramping the LED current in both directions (i.e., up and down) may not be necessary but gives two samples per LED current which may be useful for averaging. At each step, a map of voltage V1 is built (i.e., the unfiltered output of the I-to-V Converter 301). Here, Iref-Ifb decreases in table 1020 with increasing LED current, which is what causes I-to-V Converter 301 output V1 to fall, reaching 0V at step 5 (also seen in plot 1000 for the first case)

In some embodiments, the codes in LUT 307 taken at each step in this example are digital samples of V1 and are then used to determine any clipping which may have occurred in the sweep. In some embodiments, those clipped LED currents are re-run with I-DC bumped up to the next setting which is 900 nA injected straight to the photodiode (i.e., the second case of plot 1000). This bumping in I-DC and re-running of the clipped codes now gives the new V1 values of 14 through 18, these values are unclipped. The trace in the second case of plot 1000 shows the waveform of I-to-V Converter 301 stage output current after the subtraction. In this example, all six of the previously clipped readings are now within compliance of the offset cancelling circuit with a further margin of 350 nA. In some embodiments, the coarse I-DC step size is less than Iref, for example 0.75*Iref or 0.5*Iref.

Figure 11:
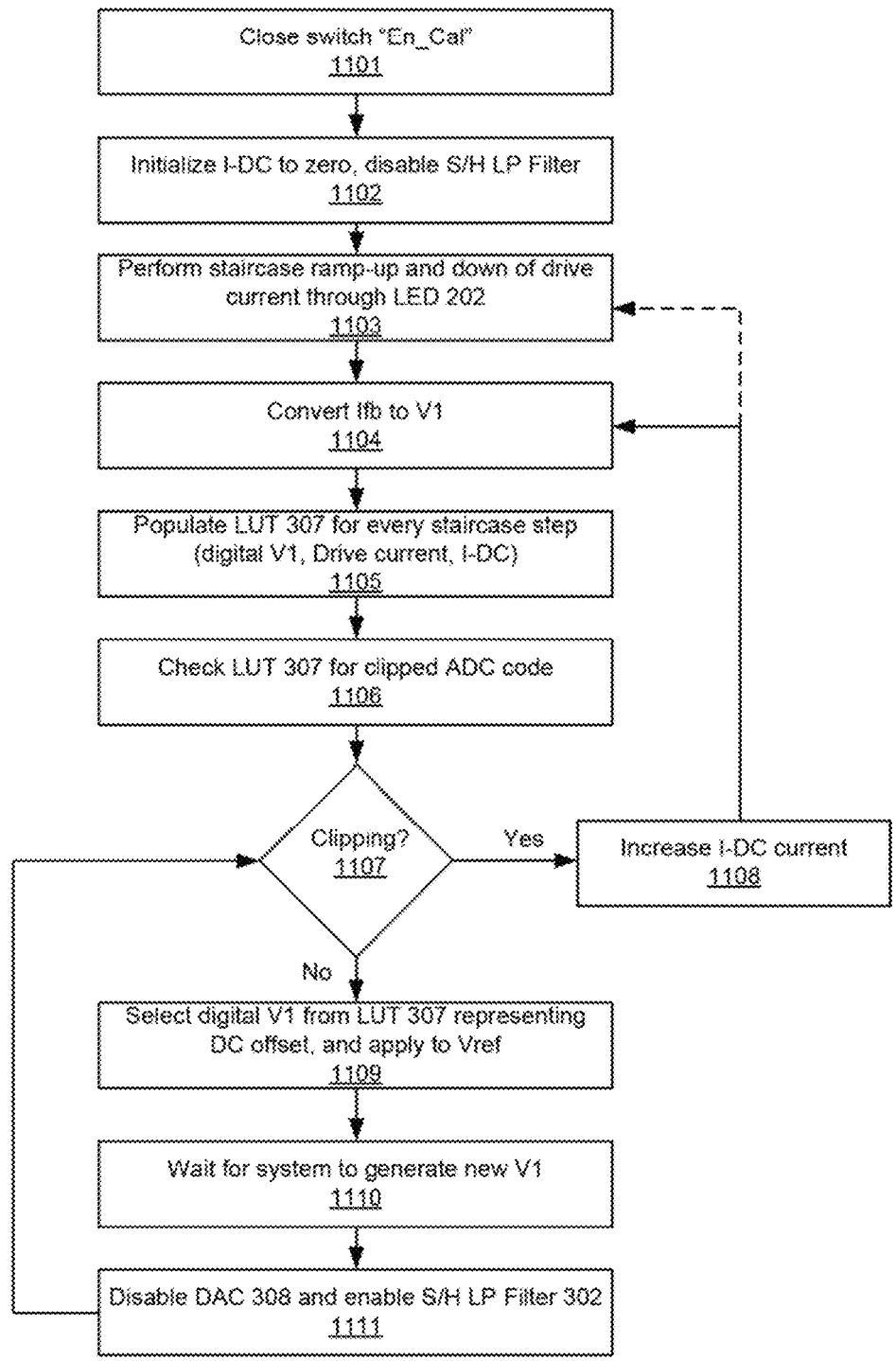
FIG. 11 illustrates a flowchart of a method for calibrating the filter settling time and improving speed of tracking and cancelling of DC offset, according to some embodiments of the disclosure.

FIG. 11 illustrates flowchart 1100 of a method for calibrating the filter settling time and improving speed of tracking and cancelling of DC offset, according to some embodiments of the disclosure. It is pointed out that those elements of FIG. 11 having the same reference numbers (or names) as the elements of any other figure can operate or function in any manner similar to that described, but are not limited to such.

Although the blocks in the flowchart with reference to FIG. 11 are shown in a particular order, the order of the actions can be modified. Thus, the illustrated embodiments can be performed in a different order, and some actions/blocks may be performed in parallel. Some of the blocks and/or operations listed in FIG. 11 are optional in accordance with certain embodiments. The numbering of the blocks presented is for the sake of clarity and is not intended to prescribe an order of operations in which the various blocks must occur. Additionally, operations from the various flows may be utilized in a variety of combinations.

At block 1101, En_Cal switch is closed. This ensures that TIA 303 can provide the photodiode current magnitude and speed during calibration. When En_Cal switch is closed, TIA 303 behaves as a unity gain buffer. At block 1102, Calibration Logic 305 initializes I-DC to zero (i.e., no current is driven by circuit block 310) and S/H LP Filter 302 is disabled (i.e., the filter does not drive Vref). At block 1103, Ramp Driver 311 begins to ramp up and/or down LED drive current for each calibration iteration. In some embodiments, the speed of ramp is many times faster than the maximum possible frequency of interference (approximately 20 Hz) in order to ensure minimal corruption to the calibration.

At block 1104, the received photodiode current Ifb is converted to a scaled voltage V1 by subtracting the photodiode current Ifb from a reference current Iref, and converting through resistor Rf (second resistor) which has a resistance value of Rf (i.e., the first resistor used in feedback loop with TIA 303 when not calibrating). At block 1105, ADC 306 converts voltage V1 to a digital representation, and LUT 307 is populated with this information (i.e., information about the digital representation of V1, LED drive current, and I-DC).

At block 1106, a finite state machine (not shown) checks the contents of LUT 307 for any clipped ADC codes (i.e., any clipping in the digital representation of V1 which may show up as all zeros or all ones in the bit stream). At block 1107, a determination is made if clipping exists. If clipping exists at the current LED current levels, then the finite state machine iteratively increases I-DC current at block 1108, and the process is repeated again (i.e., process begins again from block 1103 or 1104). The I-DC setting is stored alongside corresponding Vref (in the form of digital representation of V1) in LUT 307. Providing larger I-DC currents straight to photodiode 203 ensures a large resistance for resistor Rf can be used in TIA 303 without Vout leaving compliance.

At block 1109, the finite state machine selects the digital V1 from LUT 307 representing an estimate of DC offset to be seen in the photodiode current during normal operation. This digital V1 is converted to an analog version by DAC 308 and forced on Vref. At block 1110, the system is allowed to consume Vref forced by DAC 308 so that a new V1 is generated by I-to-V Converter 301. After waiting for a predetermined or programmable time, the process proceeds to block 1111, in accordance with some embodiments.

At block 1111, DAC 308 is disabled and S/H LP Filter 302 is enabled for normal operation. During this process, I-DC is continuously provided to reduce the DC offset and to avoid any clipping on V1. In some embodiments, TIA 303 will now pass the PPG signals at any LED current drive level without clipping or waiting for S/H LP Filter 302 to settle down. In some embodiments, the calibration process is re-performed if clipping is detected in the back end of the amplifier chain.

Figure 12:
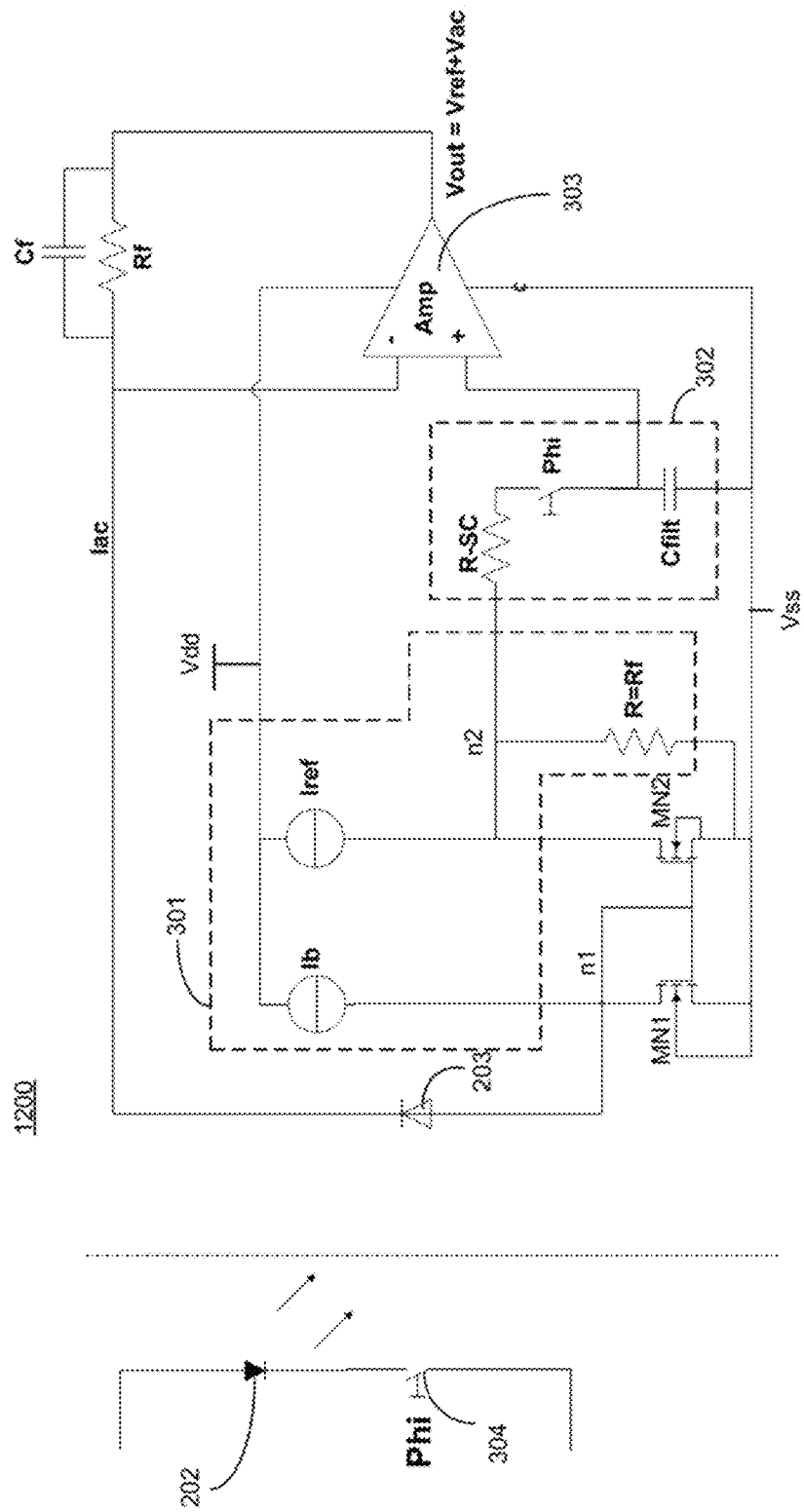
FIG. 12 illustrates a transistor-level feedforward path coupled to the non-inverting input of an amplifier, according to some embodiments of the disclosure.

FIG. 12 illustrates apparatus 1200 of transistor-level feedforward path coupled to the non-inverting input of TIA 303, according to some embodiments of the disclosure. It is pointed out that those elements of FIG. 12 having the same reference numbers (or names) as the elements of any other figure can operate or function in any manner similar to that described, but are not limited to such. So as not to obscure the embodiments, differences between FIG. 12 and FIG. 3A are described. For simplicity sake, Calibration Logic 305 is not shown in FIG. 12. In this embodiment, the copy of photodiode current is not used and instead photodiode current is directly used by I-to-V Converter 301 to generate output V1 (i.e., on node n2) for S/H LP Filter 302.

In some embodiments, I-to-V Converter 301 comprises a bias current source Ib, reference current source Iref, and replica resistor Rf coupled together as shown. In some embodiments, the bias current source Ib provides bias current Ib to n-type transistor MN1. In some embodiments, S/H LP Filter 302 comprises switching resistor and capacitor R-SC (e.g., MOS resistor) and Cfilt (e.g., a MOS capacitor), respectively, coupled together via a switch controlled by Phi.

In some embodiments, the photocurrent mirrored through n-type transistors MN1 and MN2 is subtracted from Iref and then dropped into resistor Rf (having the same resistance as the resistance of the feedback resistor Rf coupled to TIA 303). This gives a voltage of maximum value Ire*PRf, which drops as the photocurrent rises, in accordance with some embodiments. In some embodiments, the voltage V1 on node n2 (same as node V1) can be filtered with a low frequency pole to remove all components of AC signal leaving flicker noise and DC components. The voltage stored on capacitor Cfilt is then presented to the non-inverting TIA input, in accordance with some embodiments.

The effect is akin to a static Vref on the non-inverting input (of TIA 303) dropping in sympathy with increasing photodiode DC current (i.e., because Vref is scaled by resistance Rf, Vref drops by the exact amount Vout would have risen by to push the DC component back through the feedback resistor Rf). By presenting this filtered DC voltage to the non-inverting input of TIA 303, the output of TIA 303 is driven downwards by the exact amount it would have risen upwards to provide the DC offset current. As such, in some embodiments, the output voltage of TIA 303 is notionally free of the DC photodiode current but facilitates a gain of Rf exclusively to the AC photocurrent. The large DC voltage excursion that would have appeared at the output of TIA 303 now appears as a negative excursion from the reference level (i.e., (Iref-$I_{DC}$).Rf) at the non-inverting input of TIA 303, in accordance with some embodiments.

Figure 13:
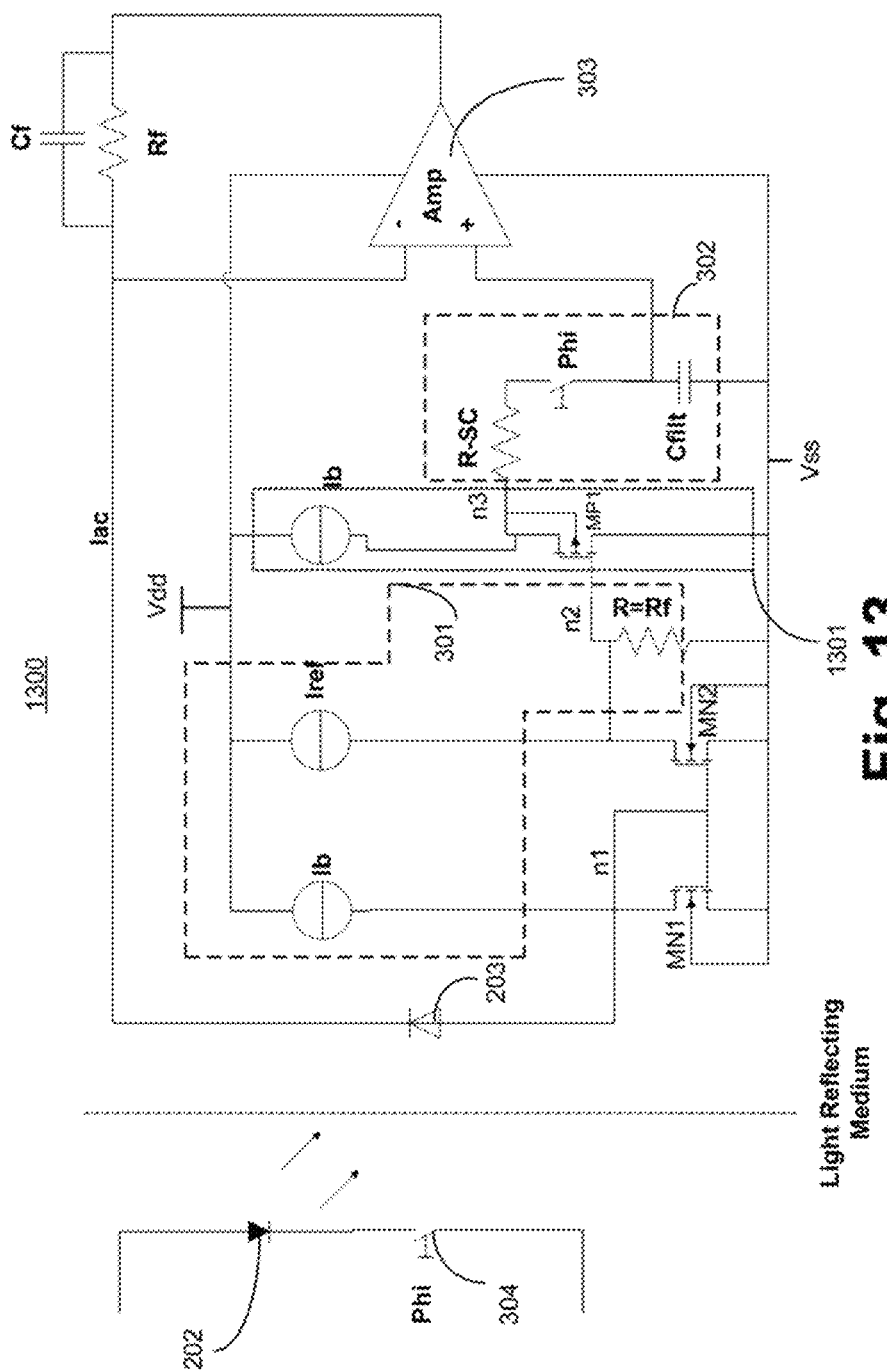
FIG. 13 illustrates a transistor-level feedforward path coupled to the non-inverting input of the amplifier, according to some other embodiments of the disclosure.

FIG. 13 illustrates apparatus 1300 of a transistor-level feedforward path coupled to the non-inverting input of the TIA, according to some other embodiments of the disclosure. It is pointed out that those elements of FIG. 13 having the same reference numbers (or names) as the elements of any other figure can operate or function in any manner similar to that described, but are not limited to such. So as not to obscure the embodiments, differences between FIG. 13 and FIG. 3A are described. For simplicity sake, Calibration Logic 305 is not shown in FIG. 13. In this embodiment, the copy of photodiode current is used instead of using photodiode current directly by I-to-V Converter 301 to generate output V1 (i.e., on node n2) for S/H LP Filter 302. Front-end 1300 is similar to front-end 300 except that a voltage-to-current (V-to-I) Converter 1301 is added as shown (and Calibration Logic 305 and associated En_Cal switch are not shown).

In some embodiments, instead of node n2 coupling directly to S/H LP Filter 302, node n2 is coupled to a gate terminal of a p-type transistor MP1. In some embodiments, the p-type transistor MP1 is coupled in series with a current source Ib. In some embodiments, this current source may not have to relate to Ib in transistor MN1. In some embodiments, the value of current Ib is determined by noise requirements, slewing on node n3, and other design parameters which may become relevant in an implementation. Because resistor R-SC may be such high impedance to get a low frequency pole, the current in Ib may not affect the RC filter too much in operation, in accordance with some embodiments.

In some embodiments, the resistor R-SC of S/H LP Filter 302 is coupled to the source terminal of transistor MP1. In some embodiments, the output voltage on node n2 of I-to-V Converter 301 is level shifted up and buffered by the transistor MP1. Such level shifting can be beneficial if the DC offset overloads I-to-V Converter 301 and sends or collapses V1 to ground (i.e., V1 clips). For example, transistor MP1 can ensure the voltage levels of the terminals or nodes of amplifier 303 do not drop below a $V_{threshold}$ and therefore the voltage across photodiode 203 stays at a $V_{threshold}$ keeping photodiode 203 reverse biased. In some embodiments, transistor MP1 also buffers the output of I-to-V Converter 301 before meeting with RC sample and hold filter 302. In some embodiments, the buffered voltage on node n3 is filtered with a large time constant using the on-die capacitor Cfilt and resistor R-SC and fed forward to the non-inverting input of TIA 303. In some embodiments, the on-die capacitor Cfilt and the resistor R-SC are part of S/H LP Filter 302.

Figure 14:
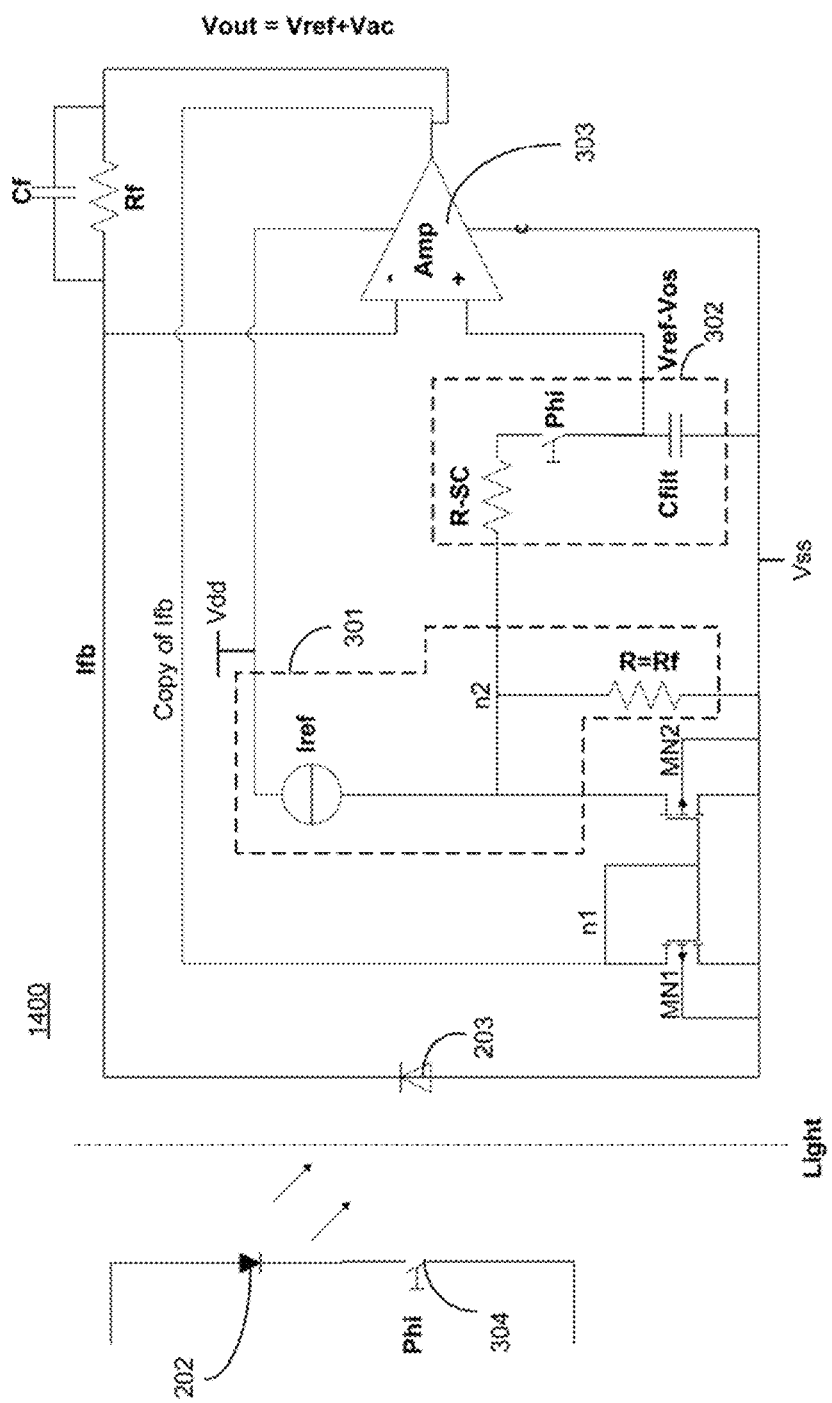
FIG. 14 illustrates a front-end of the PPG device including an amplifier and a feedforward path coupled to the non-inverting input of the amplifier, where the feedforward path uses a copy of the photodiode current, according to some other embodiments of the disclosure.

FIG. 14 illustrates apparatus 1400 of a front-end of the PPG device including TIA 303 and a feedforward path coupled to the non-inverting input of TIA 303, where the feedforward path uses a copy of the photodiode current, according to some other embodiments of the disclosure.

So as not to obscure the embodiments, differences between FIG. 14 and FIG. 3A are described. For simplicity sake, Calibration Logic 305 and associated En_Cal is not shown in FIG. 14. In this embodiment, the copy of photodiode current is used instead of using photodiode current directly by I-to-V Converter 301 to generate output V1 (i.e., on node n2) for S/H LP Filter 302.

In some embodiments, instead of transistor MN1 receiving current (Ifb) directly from photodiode 203, a copy of the photodiode current (i.e., copy of Ifb) is used to bias transistor MN1. In some embodiments, this current is mirrored from transistor MN1 to transistor MN2 and then converted to voltage on node n2. Node n2 is coupled to resistor R-SC.

While the various embodiments are described with reference to n-type current mirror for mirroring the current of photodiode 203, or for mirroring a copy of the current, the circuit implementations of various embodiments can be re-configured using p-type devices instead. This notion applies to the various embodiments (i.e., the choice of transistor type can be changed and the design can be modified accordingly without changing the essence of the embodiments). All such modifications are considered within the scope of the various embodiments.

Figures 15A, 15B:
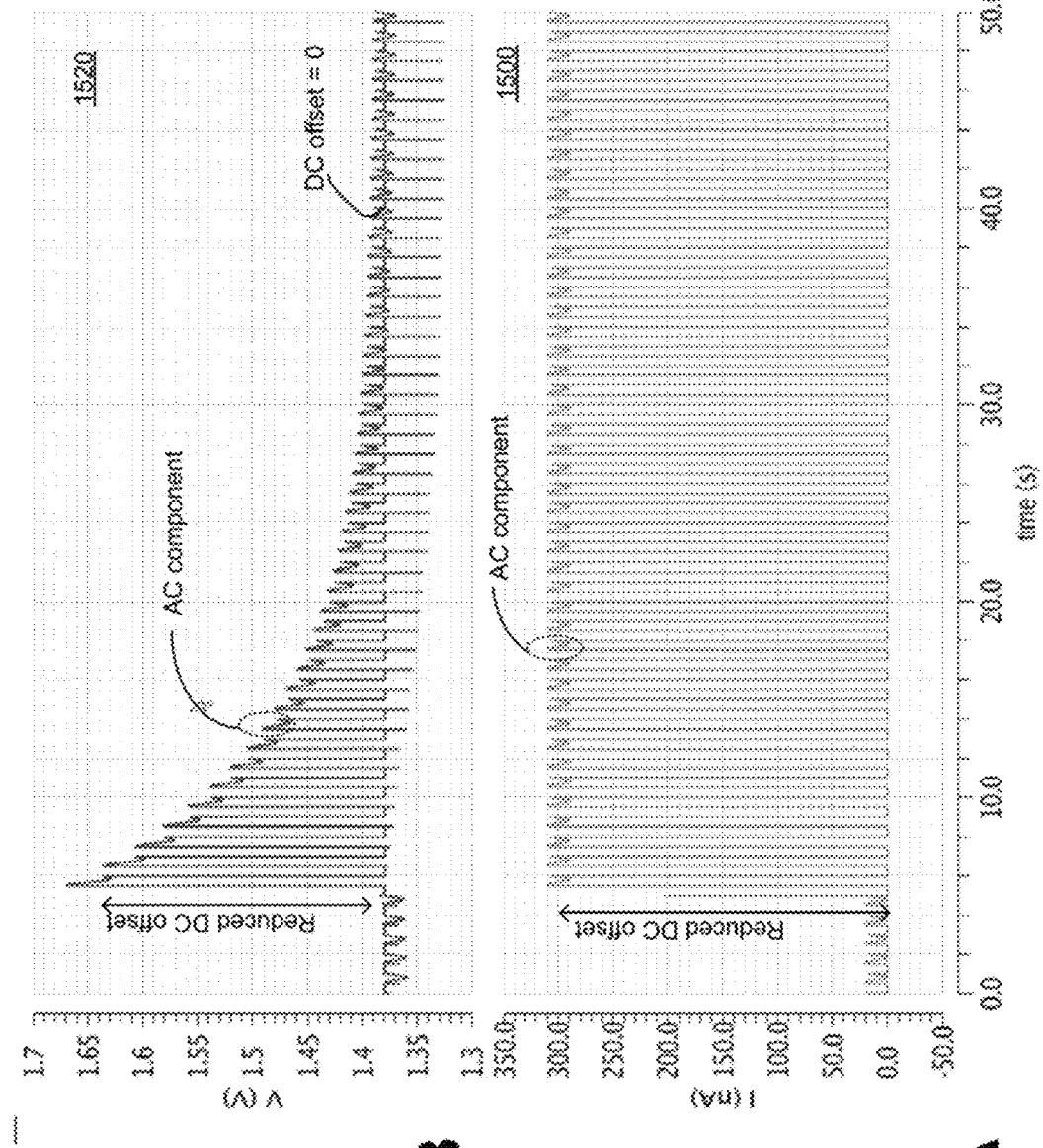
FIGS. 15A-B illustrate plots showing input current AC and DC components and cancelling of DC offset using the apparatus of various embodiments.

FIGS. 15A-B illustrate plots 1500 and 1520 showing input current AC and DC components and cancelling of DC offset using the apparatus of various embodiments. It is pointed out that those elements of FIGS. 15A-B having the same reference numbers (or names) as the elements of any other figure can operate or function in any manner similar to that described, but are not limited to such.

For plot FIG. 15A, x-axis is time in seconds and y-axis is current in nano Amperes (nA). In this example, from time 0 to about 5 seconds, there is no DC offset in the photodiode current to illustrate the ideal situation. The waveform of plot 1500 shows the DC component of the photodiode current (i.e., DC Offset) and the AC component of the photodiode current. The AC component is the signal of interest which resides on top of the DC component.

For plot FIG. 15B, x-axis is time in seconds and y-axis is voltage in Volts. In this example, from time 0 to about 5 seconds, there is no DC offset in the output of TIA 303 to illustrate the ideal situation. The waveform of plot 1520 shows the DC component (i.e., DC Offset) at the output of TIA 303 and the corresponding AC component. The apparatus of various embodiments slowly cancels the DC offset from the output voltage of TIA 303, and after about 30 seconds, the DC offset is substantially removed. The AC component is the signal of interest, and which is left over for further processing.

Figure 16:
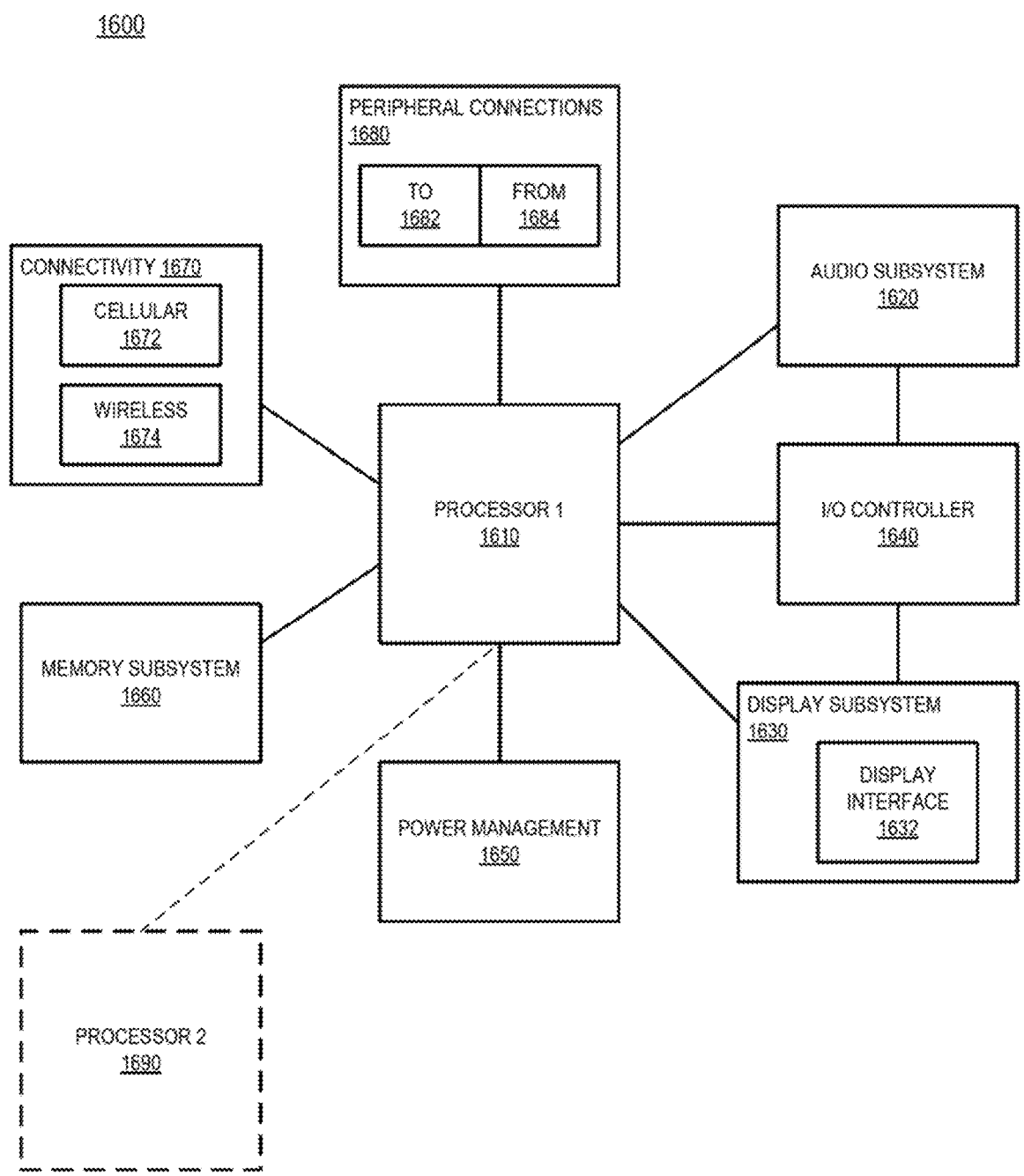
FIG. 16 illustrates a smart device or a computer system or a SoC with apparatus to calibrate filter settling time and improve speed of tracking and cancelling of DC offset, according to some embodiments.

FIG. 16 illustrates a smart device or a computer system or a SoC 1600 with apparatus to calibrate filter settling time and improve speed of tracking and cancelling of DC offset, according to some embodiments. It is pointed out that those elements of FIG. 16 having the same reference numbers (or names) as the elements of any other figure can operate or function in any manner similar to that described, but are not limited to such.

FIG. 16 illustrates a block diagram of an embodiment of a mobile device in which flat surface interface connectors could be used. In some embodiments, computing device 1600 represents a mobile computing device, such as a computing tablet, a mobile phone or smart-phone, a wireless-enabled e-reader, or other wireless mobile device. It will be understood that certain components are shown generally, and not all components of such a device are shown in computing device 1600.

In some embodiments, computing device 1600 includes a first processor 1610 with apparatus to calibrate filter settling time and improve speed of tracking and cancelling of DC offset, according to some embodiments discussed. Other blocks of the computing device 1600 may also include the apparatus to calibrate filter settling time and improve speed of tracking and cancelling of DC offset, according to some embodiments. The various embodiments of the present disclosure may also comprise a network interface within 1670 such as a wireless interface so that a system embodiment may be incorporated into a wireless device, for example, cell phone or personal digital assistant.

In one embodiment, processor 1610 (and/or processor 1690) can include one or more physical devices, such as microprocessors, application processors, microcontrollers, programmable logic devices, or other processing means. The processing operations performed by processor 1610 include the execution of an operating platform or operating system on which applications and/or device functions are executed. The processing operations include operations related to I/O (input/output) with a human user or with other devices, operations related to power management, and/or operations related to connecting the computing device 1600 to another device. The processing operations may also include operations related to audio I/O and/or display I/O.

In one embodiment, computing device 1600 includes audio subsystem 1620, which represents hardware (e.g., audio hardware and audio circuits) and software (e.g., drivers, codecs) components associated with providing audio functions to the computing device. Audio functions can include speaker and/or headphone output, as well as microphone input. In some embodiments, audio subsystem 1620 includes apparatus and/or machine executable instructions to avoid self-hearing, according to some embodiments. Devices for such functions can be integrated into computing device 1600, or connected to the computing device 1600. In one embodiment, a user interacts with the computing device 1600 by providing audio commands that are received and processed by processor 1610.

Display subsystem 1630 represents hardware (e.g., display devices) and software (e.g., drivers) components that provide a visual and/or tactile display for a user to interact with the computing device 1600. Display subsystem 1630 includes display interface 1632, which includes the particular screen or hardware device used to provide a display to a user. In one embodiment, display interface 1632 includes logic separate from processor 1610 to perform at least some processing related to the display. In one embodiment, display subsystem 1630 includes a touch screen (or touch pad) device that provides both output and input to a user.

I/O controller 1640 represents hardware devices and software components related to interaction with a user. I/O controller 1640 is operable to manage hardware that is part of audio subsystem 1620 and/or display subsystem 1630. Additionally, I/O controller 1640 illustrates a connection point for additional devices that connect to computing device 1600 through which a user might interact with the system. For example, devices that can be attached to the computing device 1600 might include microphone devices, speaker or stereo systems, video systems or other display devices, keyboard or keypad devices, or other I/O devices for use with specific applications such as card readers or other devices.

As mentioned above, I/O controller 1640 can interact with audio subsystem 1620 and/or display subsystem 1630. For example, input through a microphone or other audio device can provide input or commands for one or more applications or functions of the computing device 1600. Additionally, audio output can be provided instead of, or in addition to display output. In another example, if display subsystem 1630 includes a touch screen, the display device also acts as an input device, which can be at least partially managed by I/O controller 1640. There can also be additional buttons or switches on the computing device 1600 to provide I/O functions managed by I/O controller 1640.

In one embodiment, I/O controller 1640 manages devices such as accelerometers, cameras, light sensors or other environmental sensors, or other hardware that can be included in the computing device 1600. The input can be part of direct user interaction, as well as providing environmental input to the system to influence its operations (such as filtering for noise, adjusting displays for brightness detection, applying a flash for a camera, or other features).

In one embodiment, computing device 1600 includes power management 1650 that manages battery power usage, charging of the battery, and features related to power saving operation. Memory subsystem 1660 includes memory devices for storing information in computing device 1600. Memory can include nonvolatile (state does not change if power to the memory device is interrupted) and/or volatile (state is indeterminate if power to the memory device is interrupted) memory devices. Memory subsystem 1660 can store application data, user data, music, photos, documents, or other data, as well as system data (whether long-term or temporary) related to the execution of the applications and functions of the computing device 1600.

Elements of embodiments are also provided as a machine-readable medium (e.g., memory 1660) for storing the computer-executable instructions (e.g., instructions to implement any other processes discussed herein). The machine-readable medium (e.g., memory 1660) may include, but is not limited to, flash memory, optical disks, CD-ROMs, DVD ROMs, RAMs, EPROMs, EEPROMs, magnetic or optical cards, phase change memory (PCM), or other types of machine-readable media suitable for storing electronic or computer-executable instructions. For example, embodiments of the disclosure may be downloaded as a computer program (e.g., BIOS) which may be transferred from a remote computer (e.g., a server) to a requesting computer (e.g., a client) by way of data signals via a communication link (e.g., a modem or network connection).

Connectivity 1670 includes hardware devices (e.g., wireless and/or wired connectors and communication hardware) and software components (e.g., drivers, protocol stacks) to enable the computing device 1600 to communicate with external devices. The computing device 1600 could be separate devices, such as other computing devices, wireless access points or base stations, as well as peripherals such as headsets, printers, or other devices.

Connectivity 1670 can include multiple different types of connectivity. To generalize, the computing device 1600 is illustrated with cellular connectivity 1672 and wireless connectivity 1674. Cellular connectivity 1672 refers generally to cellular network connectivity provided by wireless carriers, such as provided via GSM (global system for mobile communications) or variations or derivatives, CDMA (code division multiple access) or variations or derivatives, TDM (time division multiplexing) or variations or derivatives, or other cellular service standards. Wireless connectivity (or wireless interface) 1674 refers to wireless connectivity that is not cellular, and can include personal area networks (such as Bluetooth, Near Field, etc.), local area networks (such as Wi-Fi), and/or wide area networks (such as WiMax), or other wireless communication.

Peripheral connections 1680 include hardware interfaces and connectors, as well as software components (e.g., drivers, protocol stacks) to make peripheral connections. It will be understood that the computing device 1600 could be a peripheral device ("to" 1682) to other computing devices, as well as have peripheral devices ("from" 1684) connected to it. The computing device 1600 commonly has a "docking" connector to connect to other computing devices for purposes such as managing (e.g., downloading and/or uploading, changing, synchronizing) content on computing device 1600. Additionally, a docking connector can allow computing device 1600 to connect to certain peripherals that allow the computing device 1600 to control content output, for example, to audiovisual or other systems.

In addition to a proprietary docking connector or other proprietary connection hardware, the computing device 1600 can make peripheral connections 1680 via common or standards-based connectors. Common types can include a Universal Serial Bus (USB) connector (which can include any of a number of different hardware interfaces), DisplayPort including MiniDisplayPort (MDP), High Definition Multimedia Interface (HDMI), Firewire, or other types.

Reference in the specification to "an embodiment," "one embodiment," "some embodiments," or "other embodiments" means that a particular feature, structure, or characteristic described in connection with the embodiments is included in at least some embodiments, but not necessarily all embodiments. The various appearances of "an embodiment," "one embodiment," or "some embodiments" are not necessarily all referring to the same embodiments. If the specification states a component, feature, structure, or characteristic "may," "might," or "could" be included, that particular component, feature, structure, or characteristic is not required to be included. If the specification or claim refers to "a" or "an" element, that does not mean there is only one of the elements. If the specification or claims refer to "an additional" element, that does not preclude there being more than one of the additional element.

Furthermore, the particular features, structures, functions, or characteristics may be combined in any suitable manner in one or more embodiments. For example, a first embodiment may be combined with a second embodiment anywhere the particular features, structures, functions, or characteristics associated with the two embodiments are not mutually exclusive.

While the disclosure has been described in conjunction with specific embodiments thereof, many alternatives, modifications and variations of such embodiments will be apparent to those of ordinary skill in the art in light of the foregoing description. For example, other memory architectures e.g., Dynamic RAM (DRAM) may use the embodiments discussed. The embodiments of the disclosure are intended to embrace all such alternatives, modifications, and variations as to fall within the broad scope of the appended claims.

In addition, well known power/ground connections to integrated circuit (IC) chips and other components may or may not be shown within the presented figures, for simplicity of illustration and discussion, and so as not to obscure the disclosure. Further, arrangements may be shown in block diagram form in order to avoid obscuring the disclosure, and also in view of the fact that specifics with respect to implementation of such block diagram arrangements are highly dependent upon the platform within which the present disclosure is to be implemented (i.e., such specifics should be well within purview of one skilled in the art). Where specific details (e.g., circuits) are set forth in order to describe example embodiments of the disclosure, it should be apparent to one skilled in the art that the disclosure can be practiced without, or with variation of, these specific details. The description is thus to be regarded as illustrative instead of limiting.

The following examples pertain to further embodiments. Specifics in the examples may be used anywhere in one or more embodiments. All optional features of the apparatus described herein may also be implemented with respect to a method or process.

For example, an apparatus comprising: an amplifier to receive a reference voltage; and calibration logic which is operable to receive a first voltage and to provide the reference voltage to the amplifier, wherein the calibration logic is operable to generate a look-up table (LUT) that maps the first voltage to a drive current. In some embodiments, the apparatus comprises: a current source to generate a first current according to the drive current provided to a light source; and a current-to-voltage converter to convert the first current or a copy of the first current to the first voltage, wherein the first voltage is proportional to a resistance.

In some embodiments, the amplifier is to receive the reference voltage according to the first voltage, wherein the reference voltage is received at a non-inverting input of the amplifier, and wherein the amplifier has an inverting input which acts to sum to zero currents at the inverting input. In some embodiments, the calibration logic comprises: an analog-to-digital converter (ADC) to receive the first voltage and to provide a digital representation of the first voltage, wherein the digital representation is stored in the LUT; and a digital-to-analog converter (DAC) to convert the digital representation of the first voltage to the reference voltage.

In some embodiments, the DAC is operable to enable itself during a calibration mode and to disable itself during a normal operation mode. In some embodiments, the first current has AC and DC components, and wherein the first voltage has AC and DC components that correspond to the AC and DC components of the first current. In some embodiments, the apparatus comprises a sample-and-hold circuit which is operable to filter the AC component from the first voltage and which is to provide an output, which is the reference voltage with the DC component, when the calibration logic is disabled.

In some embodiments, comprises: a first resistor coupled to an output of the amplifier and a non-inverting input of the amplifier; and a switch which is operable to electrically short the first resistor during a calibration mode. In some embodiments, wherein the first resistor has a resistance which is substantially equal to a resistance of a second resistor of the current-to-voltage converter. In some embodiments, the current-to-voltage converter is to cause the output of the sample-and-hold circuit to lower in voltage level as the DC component of the first current increases.

In some embodiments, comprises a voltage-to-current converter to convert the output of the sample-and-hold circuit to a second current such that slewing in the amplifier is reduced. In some embodiments, the voltage-to-current converter is to convert the output of the sample-and-hold circuit to the second current at a second phase of the switching current. In some embodiments, the first phase has a duration proportional to a duration the current source generates the first current, and wherein the second phase has a duration which is proportional to a duration the current source does not generate the first current.

In some embodiments, the sample-and-hold circuit is operable to sample the first voltage at a first phase of a switching signal. In some embodiments, a ramp driver to increase or decrease the drive current according to a control signal from the calibration logic.

In another example, an apparatus is provided which comprises: an amplifier to receive a reference voltage according to a first voltage, wherein the reference voltage is received at a non-inverting input of the amplifier, and wherein the amplifier has an inverting input which acts to sum to zero currents at the inverting input; and calibration logic which is operable to receive the first voltage and to provide the reference voltage and a DC current which is added to the first current, wherein the calibration logic is operable to generate a look-up table (LUT) that maps the first voltage to a drive current and the DC current.

In some embodiments, the apparatus comprises: a current source to generate the first current according to the drive current provided to a light source; and a current-to-voltage converter to convert the first current or a copy of the first current to the first voltage which is proportional to a resistance. In some embodiments, the calibration logic comprises: an analog-to-digital converter (ADC) to receive the first voltage and to provide a digital representation of the first voltage, wherein the digital representation is stored in the LUT; and switching logic which is operable by the digital representation of the first voltage.

In some embodiments, the calibration logic comprises a plurality of transistors such that at least one of the transistors is coupled in series with a switch which is controllable by the switching logic, and wherein the DC current is provided for adding to the first current when the switch is closed. In some embodiments, the calibration logic comprises a digital-to-analog converter (DAC) to convert the digital representation of the first voltage to the reference voltage, wherein the digital representation of the first voltage is used by the switching logic to determine which transistors of the plurality of transistors to turn on via their respective switches.

In another example, a wearable device is provided which comprises: a light source to provide light to a media according to a drive current; a current source to detect a version of the light from the media and, from the version of the light, is to generate a current having AC and DC components; an offset cancellation apparatus to receive the current, the offset cancellation apparatus including: a current-to-voltage converter to convert the current or a copy of the current to a voltage proportional to a resistance; and an amplifier to receive a reference voltage according to the voltage from the current-to-voltage converter, wherein the amplifier is to also receive the current from the photodiode; and calibration logic which is operable to receive the voltage and to provide the reference voltage, wherein the calibration logic is operable to generate a look-up table (LUT) that maps the voltage to the drive current; and a processing intellectual property (IP) block to receive a filtered version of an output of the amplifier and to determine a condition of the media according to the output of the amplifier.

In some embodiments, wearable device comprises a wireless interface for allowing the processing IP block to communicate with another device. In some embodiments, the wearable device comprises: a level shifter to level shift the output of the amplifier to a lower voltage level; a track-and-hold circuit to track the level-shifted output and then to hold it; and a gain stage with a low pass filter, wherein the gain stage is to amplify the output of the track-and-hold circuit and to filter the amplified output.

In some embodiments, the wearable device comprises an analog-to-digital converter to convert the filtered amplified output to a digital representation which is the filtered version of the output voltage provided to the processing IP block. In some embodiments, the wearable device comprises a light source driver, wherein the processing IP block is operable to adjust intensity of the light emitted by the light source. In some embodiments, the media is part of a living body, and wherein the condition is a heartbeat.

In another example, a method is provided which comprises: receiving, by an amplifier, a reference voltage; receiving a first voltage; providing the reference voltage to the amplifier; and generating a look-up table (LUT) that maps the first voltage to a drive current. In some embodiments, the method comprises: generating a first current according to the drive current provided to a light source; and converting the first current or a copy of the first current to the first voltage, wherein the first voltage is proportional to a resistance.

In some embodiments, receiving, by the amplifier, the reference voltage is according to the first voltage, wherein the reference voltage is received at a non-inverting input of the amplifier, and wherein the amplifier has an inverting input which acts to sum to zero currents at the inverting input. In some embodiments, the method comprises: receiving the first voltage; providing a digital representation of the first voltage; storing the digital representation in the LUT; and converting, by a digital-to-analog converter (DAC), the digital representation of the first voltage to the reference voltage.

In some embodiments, the method comprises: enabling the DAC during a calibration mode; and disabling the DAC during a normal operation mode. In some embodiments, the first current has AC and DC components, and wherein the first voltage has AC and DC components that correspond to the AC and DC components of the first current. In some embodiments, the method comprises: filtering, in the normal operation mode, the AC component from the first voltage and providing a filtered output, which is the reference voltage with the DC component.

In some embodiments, the method comprises: electrically shorting a first resistor during the calibration mode, wherein the first resistor is coupled to an output of the amplifier and a non-inverting input of the amplifier. In some embodiments, the first resistor has a resistance which is substantially equal to a resistance of a second resistor of a current-to-voltage converter.

In some embodiments, the method comprises causing the filtered output to lower in voltage level as the DC component of the first current increases. In some embodiments, the method comprises converting the filtered output to a second current such that slewing in the amplifier is reduced. In some embodiments, the method comprises converting the filtered output to the second current is performed at a second phase of a clock. In some embodiments, the first phase has a duration proportional to a duration the current source generates the first current, and wherein the second phase has a duration which is proportional to a duration the current source does not generate the first current. In some embodiments, the method comprises: sampling the first voltage at a first phase of the clock. In some embodiments, the method comprises increasing or decreasing the drive current according to a control signal.

In another example, an apparatus is provided which comprises: means for receiving, by an amplifier, a reference voltage; means for receiving a first voltage; means for providing the reference voltage to the amplifier; and means for generating a look-up table (LUT) that maps the first voltage to a drive current. In some embodiments, the apparatus comprises: means for generating a first current according to the drive current provided to a light source; and means for converting the first current or a copy of the first current to the first voltage, wherein the first voltage is proportional to a resistance.

In some embodiments, the means for receiving, by the amplifier, the reference voltage is according to the first voltage, wherein the reference voltage is received at a non-inverting input of the amplifier, and wherein the amplifier has an inverting input which acts to sum to zero currents at the inverting input. In some embodiments, the apparatus comprises: means for receiving the first voltage; means for providing a digital representation of the first voltage; means for storing the digital representation in the LUT; and means for converting, by a digital-to-analog converter (DAC), the digital representation of the first voltage to the reference voltage.

In some embodiments, the apparatus comprises: means for enabling the DAC during a calibration mode; and means for disabling the DAC during a normal operation mode. In some embodiments, the first current has AC and DC components, and wherein the first voltage has AC and DC components that correspond to the AC and DC components of the first current. In some embodiments, the apparatus comprises: means for filtering, in the normal operation mode, the AC component from the first voltage and providing a filtered output, which is the reference voltage with the DC component.

In some embodiments, the apparatus comprises: means for electrically shorting a first resistor during the calibration mode, wherein the first resistor is coupled to an output of the amplifier and a non-inverting input of the amplifier. In some embodiments, the first resistor has a resistance which is substantially equal to a resistance of a second resistor of a current-to-voltage converter. In some embodiments, the apparatus comprises means for causing the filtered output to lower in voltage level as the DC component of the first current increases.

In some embodiments, the apparatus comprises means for converting the filtered output to a second current such that slewing in the amplifier is reduced. In some embodiments, means for converting the filtered output to the second current is performed at a second phase of a clock. In some embodiments, the first phase has a duration proportional to a duration the current source generates the first current, and wherein the second phase has a duration which is proportional to a duration the current source does not generate the first current.

In some embodiments, the apparatus comprises means for sampling the first voltage at a first phase of the clock. In some embodiments, the apparatus comprises means for increasing or decreasing the drive current according to a control signal.

An abstract is provided that will allow the reader to ascertain the nature and gist of the technical disclosure. The abstract is submitted with the understanding that it will not be used to limit the scope or meaning of the claims. The following claims are hereby incorporated into the detailed description, with each claim standing on its own as a separate embodiment.

We claim:

1. An apparatus comprising:
   an amplifier to receive a reference voltage;
   calibration logic which is configured to receive a first voltage and to provide the reference voltage to the amplifier, wherein the calibration logic is configured to generate a look-up table (LUT) that maps the first voltage to a drive current;
   a current source to generate a first current in accordance with the drive current; and
   a current-to-voltage converter to convert the first current or a copy of the first current to the first voltage, wherein the first voltage is proportional to a resistance.

2. The apparatus of claim 1, wherein the amplifier is to receive the reference voltage in accordance with the first voltage, wherein the reference voltage is received at a first input of the amplifier, and wherein the amplifier has second input which acts to sum to zero currents at the inverting input.

3. The apparatus of claim 1, wherein the calibration logic comprises:
   an analog-to-digital converter (ADC) to receive the first voltage and to provide a digital representation of the first voltage, wherein the digital representation is stored in the LUT; and
   a digital-to-analog converter (DAC) to convert the digital representation of the first voltage to the reference voltage.

4. The apparatus of claim 3, wherein the DAC is operable to enable itself during a calibration mode and to disable itself during a normal operation mode.

5. The apparatus of claim 1, wherein the first current has AC and DC components, and wherein the first voltage has AC and DC components that correspond to the AC and DC components of the first current.

6. The apparatus of claim 5 comprises a sample-and-hold circuit which is to filter the AC component from the first voltage and which is to provide an output, which is the reference voltage with the DC component, when the calibration logic is disabled.

7. The apparatus of claim 6 comprises:
   a first resistor coupled to an output of the amplifier and the first input of the amplifier; and
   a switch which is to electrically short the first resistor during a calibration mode.

8. The apparatus of claim 7, wherein the current-to-voltage converter comprises a resistor, and wherein the first resistor has a resistance, which is substantially equal to a resistance of the resistor of the current-to-voltage converter.

9. The apparatus of claim 8, wherein the current-to-voltage converter is configured to cause the output of the sample-and-hold circuit to lower in voltage level as the DC component of the first current increases.

10. The apparatus of claim 9 comprises a voltage-to-current converter configured to convert the output of the sample-and-hold circuit to a second current such that slewing in the amplifier is reduced.

11. The apparatus of claim 10, wherein the voltage-to-current converter is configured to convert the output of the sample-and-hold circuit to the second current at a second phase of a switchable current.

12. The apparatus of claim 11, wherein the first phase has a duration proportional to a duration the current source generates the first current, and wherein the second phase has a duration which is proportional to a duration the current source does not generate the first current.

13. The apparatus of claim 6, wherein the sample-and-hold circuit is to sample the first voltage at a first phase of a switchable signal.

14. The apparatus of claim 1 comprises a ramp driver configured to increase or decrease the drive current in accordance with a control signal from the calibration logic.

15. An apparatus comprising:
   an amplifier to receive a reference voltage in accordance with a first voltage, wherein the reference voltage is received at a first input of the amplifier, and wherein the amplifier has a second input which acts to sum to zero currents at the second input;
   calibration logic which is configured to receive the first voltage and to provide the reference voltage and a DC current which is added to the first current, wherein the calibration logic is configured to generate a look-up table (LUT) that maps the first voltage to a drive current and the DC current;
   a current source to generate the first current in accordance with the drive current; and
   a current-to-voltage converter to convert the first current or a copy of the first current to the first voltage which is proportional to a resistance.

16. The apparatus of claim 15, wherein the calibration logic comprises:
   an analog-to-digital converter (ADC) to receive the first voltage and to provide a digital representation of the first voltage, wherein the digital representation is stored in the LUT; and
   switch logic which is by the digital representation of the first voltage.

17. The apparatus of claim 16, wherein the calibration logic comprises a plurality of transistors such that at least one of the transistors is coupled in series with a switch which is controllable by the switch logic, and wherein the DC current is provided to add to the first current when the switch is closed.

18. The apparatus of claim 17, wherein the calibration logic comprises a digital-to-analog converter (DAC) to convert the digital representation of the first voltage to the reference voltage, wherein the digital representation of the first voltage is used by the switch logic to determine which transistors of the plurality of transistors to turn on via their respective switches.

* * * * *